(12) United States Patent
Toth et al.

(10) Patent No.: US 9,011,820 B2
(45) Date of Patent: Apr. 21, 2015

(54) SCREENING TOOL FOR ANTIVIRAL AGENTS

(75) Inventors: Karoly Toth, St. Louis, MO (US); William S. M. Wold, Chesterfield, MO (US)

(73) Assignee: Saint Louis University, St. Louis, MO (US)

(*) Notice: Subject to any disclaimer, the term of this patent is extended or adjusted under 35 U.S.C. 154(b) by 764 days.

(21) Appl. No.: 12/124,807

(22) Filed: May 21, 2008

(65) Prior Publication Data

US 2009/0017448 A1 Jan. 15, 2009

Related U.S. Application Data

(60) Provisional application No. 60/939,184, filed on May 21, 2007.

(51) Int. Cl.
| | |
|---|---|
| A61K 49/00 | (2006.01) |
| A61K 39/235 | (2006.01) |
| C12Q 1/70 | (2006.01) |
| C12N 15/00 | (2006.01) |
| G01N 33/50 | (2006.01) |
| C12N 7/00 | (2006.01) |
| C12N 15/86 | (2006.01) |

(52) U.S. Cl.
CPC .............. *G01N 33/5088* (2013.01); *C12N 7/00* (2013.01); *C12N 15/86* (2013.01); *C12N 2710/10343* (2013.01); *G01N 2333/075* (2013.01)

(58) Field of Classification Search
None
See application file for complete search history.

(56) References Cited

PUBLICATIONS

Lenaerts et al., Mouse Adenovirus Type 1 Infection in SCID Mice: an Experimental Model for Antiviral Therapy of Systemic Adenovirus Infections, 2005, Antimicrobial Agents and Chemotherapy, vol. 49, No. 11, pp. 4689-4699.*
Lamfers et al., Cyclophosphamide Increases Transgene Expression Mediated by an Oncolytic Adenovirus in Glioma-Bearing Mice Monitored by Bioluminescence Imaging, 2006, Molecular Therapy, vol. 14, No. 6, pp. 779-788.*
Hjorth et al., A new hamster model for adenoviral vaccination Brief Report, 1988, Archives of Virology, vol. 100, pp. 279-283.*
Romanowski and Gordon, Effects of Diclofenac or Ketorolac on the Inhibitory Activity of Cidofovir in the Ad5/NZW Rabbit Model, 2001, Investigative Ophthalmology and Visual Science, vol. 42, No. 1, pp. 158-162.*
Nakatani et al., Assessment of efficiency and safety of adenovirus mediated gene transfer into normal and damaged murine livers, 2000, Gut, vol. 47, pp. 563-570.*
Ginsberg et al., A mouse model for investigating the molecular pathogenesis of adenovirus pneumonia, 1991, PNAS, vol. 88, pp. 1651-1655.*
Aldern, K. A., S. L. Ciesla, K. L. Winegarden, and K. Y. Hostetler. 2003. Increased antiviral activity of 1-O-hexadecyloxypropyl-[2-(14)C]cidofovir in MRC-5 human lung fibroblasts is explained by unique cellular uptake and metabolism. Molecular Pharmacology, vol. 63, No. 3, pp. 678-681, Copyright by The American Society for Pharmacology and Experimental Therapeutics, U.S.A.
Beadle, J. R., C. Hartline, K. A. Aldern, N. Rodriguez, E. Harden, E. R. Kern, and K. Y. Hostefler. 2002. Alkoxyalkyl esters of cidofovir and cyclic cidofovir exhibit multiple-log enhancement of antiviral activity against cytomegalovirus and herpesvirus replication in vitro. Antimicrobial Agents and Chemogherapy, vol. 46, No. 8, pp. 2381-2386, Copyright by American Society for Microbiology.
Bidanset, D. J., J. R. Beadle, W. B. Wan, K. Y. Hostetler, and E. R. Kern. 2004. Oral activity of ether lipid ester prodrugs of cidofovir against experimental human cytomegalovirus infection. The Journal of Infectious Diseases, vol. 190, pp. 499-503, Copyright by the Infectious Diseases Society of America.
Bordigoni, P., A. S. Carret, V. Venard, F. Witz, and A. Le Faou. 2001. Treatment of adenovirus infections in patients undergoing allogeneic hematopoietic stem cell transplantation. Clinical Infectious Diseases, vol. 32, pp. 1290-1297, copyright by the Infectious Diseases Society of America.
Buller, R. M., G. Owens, J. Schriewer, L. Melman, J. R. Beadle, and K. Y. Hostetler. 2003. Efficacy of oral active ether lipid analogs of cidofovir in a lethal mousepox model. Virology 318, pp. 474-481, Copyright by Elsevier Inc.
Carter, B. A., S. J. Karpen, R. E. Quiros-Tejeira, I. F. Chang, B. S. Clark, G. J. Demmler, H. E. Heslop, J. D. Scott, P. Seu, and J. A. Goss. 2002. Intravenous Cidofovir therapy for disseminated adenovirus in a pediatric liver transplant recipient. Transplantation vol. 74, No. 7, pp. 1050-1052, Copyright by Lippincott Williams & Wilkins.
Ciesla, L.L., J. Trahan, W.B. Wan, J.R. Beadle, K.A. Aldern, G.R. Painter, and K.Y. Hostetler. 2003. Exterification of cidofovir with alkoxyalkanola increases oral bioavailability and diminishes drug accumulation in kidney. Antiviral Research, vol. 59, pp. 163-171, Published by Elsevier B.V.
De Clercq, E. and A. Holy. 2005. Acyclic nucleoside phosphonates: a key class of antiviral drugs. Nature Reviews Drug Discovery, vol. 4, pp. 928-940, Copyright by Nature Publishing Group.
Doronin, K., M. Kuppuswamy, K. Toth, A. E. Tollefson, P. Krajcsi, V. Krougliak, and W. S. M. Wold. 2001. Tissue-specific, tumor-selective, replication-competent adenovirus vector for cancer gene therapy. Journal of Virology, vol. 75, No. 7, pp. 3314-3324, Copyright by American Society for Microbiology.
Doronin, K., K. Toth, M. Kuppuswamy, P. Krajcsi, A. E. Tollefson, and W. S. M. Wold. 2003. Overexpression of the ADP (~3-11.6K) protein increases cell lysis and spread of adenovims. Virology 305, pp. 378-387, Copyright by Elsevier Science (USA).

(Continued)

*Primary Examiner* — Benjamin P Blumel
(74) *Attorney, Agent, or Firm* — Parker Highlander PLLC

(57) ABSTRACT

A method is provided for screening anti-adenovirus agents. The method includes reducing the activation of the immune system of a small mammal, administering a human adenovirus vector to the small mammal, monitoring the tumor cells in the mammal, and analyzing infectious virus units within the tumor cells and the organs of the small mammal. Specifically, the immune system of the small mammal is suppressed using cyclophosphamide. The small mammal may be, but is not limited to, one of the following: mice, rabbits, cotton rats, hamsters, rats, and other small rodents.

7 Claims, 17 Drawing Sheets

(56) References Cited

PUBLICATIONS

Doronin, K., K. Toth, M. Kuppuswamy, P. Ward, A. E. Tollefson, and W. S. M. Wold. 2000. Tumor-specific, replication-competent adenovirus vectors overexpressing the Adenovirus Death Protein. Journal of Virology, vol. 74, No. 13, pp. 6147-6155, Copyright by American Society for Microbiology.

Fanourgiakis, P., A. Georgala, M. Vekemans, A. Triffet, J. M. De Bruyn, V. Duchateau, P. Martiat, E. De Clercq, R. Snoeck, E. Wollants, A. Rector, M. Van Ranst, and M. Aoun. 2005. Intravesical instillation of cidofovir in the treatment of hemorrhagic cystitis caused by adenovirus type 11 in a bone marrow transplant recipient. Clinical Infectious Diseases, vol. 40, pp. 199-201, copyright by the Infectious Diseases Society of America (2004).

Fianchi, L., A. Scardocci, P. Cattani, T. Tartaglione, and L. Pagano. 2003. Adenovirus meningoencephalitis in a patient with large B-cell lymphoma. Annals of Hematology, vol. 82, pp. 313-315, copyright by Springer-Verlag.

Habib, N. A., R. Mitry, P. Seth, M. Kuppuswamy, K. Doronin, K. Toth, P. Krajcsi, A. E. Tollefson, and W. S. M. Wold. 2002. Adenovirus replication-competent vectors (KD 1, KD3) complement the cytotoxicity and transgene expression from replication-defective vectors (AdGFP, Ad-Luc). Cancer Gene Therapy, vol. 9, pp. 651-654, copyright by Nature Publishing Group.

Hartline, C. B., K. M. Gustin, W. B. Wan, S. L. Ciesla, J. R. Beadle, K. Y. Hostetler, and E. R. Kern. 2005. Ether lipid-ester prodrugs of acyclic nucleoside phosphonates: activity against adenovirus replication in vitro. The Journal of Infectious Diseases, vol. 191, pp. 396-399, copyright by the Infectious Diseases of America (2004).

Hatakeyama, N., N. Suzuki, T. Kudoh, T. Hori, N. Mizue, and H. Tsutsumi. 2003. Successful cidofovir treatment of adenovirus-associated hemorrhagic cystitis and renal dysfunction after allogenic bone marrow transplant. The Pediatric Infectious Disease Journal, vol. 22, No. 10, pp. 928-929, copyright by Lippincott Williams & Wilkins.

Hillenkamp, J., T. Reinhard, R. S. Ross, D. Bohringer, O. Cartsburg, M. Roggendorf, E. De Clercq, E. Godehardt, and R. Sundmacher. 2001. Topical treatment of acute adenoviral keratoconjunctivitis with 0.2% cidofovir and 1% cyclosporine: a controlled clinical pilot study. Archives of Ophthalmology, vol. 119, pp. 1487-1491, copyright by American Medical Association.

Hillenkamp, J., T. Reinhard, R. S. Ross, D. Bohringer, O. Cartsburg, M. Roggendorf, E. De Clercq, E. Godehardt, and R. Sundmacher. 2002. The effects of cidofovir 1% with and without cyclospodn a 1% as a topical treatment of acute adenoviral keratoconjunctivitis: a controlled clinical pilot study. Ophthalmology, vol. 109, pp. 845-850, copyright by American Academy of Opthamology.

Hjorth, R. N., G. M. Bonde, W. A. Pierzchala, S. K. Vernon, F. P. Wiener, M. H. Levner, M. D. Lubeck, and P. P. Hung. 1988. A new hamster model for adenoviral vaccination. Archives of Ophthalmology, vol. 100, pp. 279-283, copyright by Springer-Verlag.

Hoffman, J. A., A. J. Shah, L. A. Ross, and N. Kapoor. 2001. Adenoviral infections and a prospective trial of cidofovir in pediatric hematopoietic stem cell transplantation. Biology of Blood and Marrow Transplantation, vol. 7, pp. 388-394, copyright by American Society for Blood and Marrow Transplantation.

Hostetler, K. Y., J. R. Beadle, J. Trahan, K. A. Aldern, G. Owens, J. Schriewer, L. Melman, and R. M. Buller. 2007. Oral 1-O-octadecyl-2-O-benzyl-sn-glycero-3-cidofovir targets the lung and is effective against a lethal respiratory challenge with ectromelia virus in mice. Antiviral Research, vol. 73, No. 3, pp. 212-218.

Kampmann, B., D. Cubitt, T. Walls, P. Naik, M. Depala, S. Samarasinghe, D. Robson, A. Hassan, K. Rao, H. Gaspar, G. Davies, A. Jones, C. Cale, K. Gilmour, M. Real, M. Foo, N. Bennett-Rees, A. Hewitt, P. Amrolia, and P. Veys. 2005. Improved outcome for children with disseminated adenoviral infection following allogeneic stem cell transplantation. British Journal of Haematology, vol. 130, pp. 595-603, copyright by Blackwell Publishing Ltd.

Kaneko, H., S. Mori, O. Suzuki, T. Iida, S. Shigeta, M. Abe, S. Ohno, K. Aoki, and T. Suzutani. 2004. The cotton rat model for adenovirus ocular infection: antiviral activity of cidofovir. Antiviral Research, vol. 61, pp. 63-66, copyright by Elsevier B.V. (2003).

Kern, E. R., D. J. Collins, W. B. Wan, J. R. Beadle, K. Y. Hostetler, and D. C. Quenelle. 2004. Oral treatment of murine cytomegalovirus infections with ether lipid esters of cidofovir. Antimicrobial Agents and Chemotherapy, vol. 48, No. 9, pp. 3516-3522, copyright by American Society for Microbiology.

Kinchington, P. R., E. G. Romanowski, and G. Y. Jerold. 2005. Prospects for adenovirus antivirals. Journal of Antimicrobial Chemotherapy, vol. 55, pp. 424-429, copyright by the Author.

Kojaoghlanian, T., P. Flomenberg, and M. S. Horwitz. 2003. The impact of adenovirus infection on the immunocomprolnised host. Reviews in Medical Virology, vol. 13, pp. 155-171, copyright by John Wiley & Sons, Ltd.

Kuhl, U., M. Pauschinger, P. L. Schwimmbeck, B. Seeberg, C. Lober, M. Noutsias, W. Poller, and H. P. Schultheiss. 2003. Interferon-beta treatment eliminates cardiotropic viruses and improves left ventricular function in patients with myocardial persistence of viral genomes and left ventricular dysfunction. Circulation 107, pp. 2793-2798, copyright by American Heart Association, Inc.

Kuppuswamy, M., J. F. Spencer, K. Doronin, A. E. Tollefson, W. S. Wold, and K. Toth. 2005. Oncolytic adenovirus that overproduces ADP and replicates selectively in tumors due to hTERT promoter-regulated E4 gene expression. Gene Therapy, vol. 12, pp. 1608-1617, copyright by Nature Publishing Group.

Leen, A. M., C. M. Bollard, G. D. Myers, and C. M. Rooney. 2006. Adenoviral infections in hematopoietic stem cell transplantation. Biology of Blood Marrow Transplantation, vol. 12, pp. 243-251, copyright by American Society for Blood and Marrow Transplantation.

Legrand, F., D. Berrebi, N. Houhou, F. Freymuth, A. Faye, M. Duval, J. F. Mougenot, M. Peuchmaur, and E. Vilmer. 2001. Early diagnosis of adenovirus infection and treatment with cidofovir after bone marrow transplantation in children. Bone Marrow Transplantation, vol. 27, pp. 621-626, copyright by Nature Publishing Group.

Lichtenstein, D. L., K. Toth, K. Doronin, Tollefson A.E., and W. S. M. Wold. 2004. Functions and mechanisms of action of the adenovirus E3 proteins. International Reviews of Immunology, vol. 23, pp. 75-111, copyright by Taylor & Francis Inc.

Ljungman, P. 2004. Treatment of adenovirus infections in the immunocompromised host. European Journal of Clinical Microbiology & Infectious Diseases, vol. 23, pp. 583-588, copyright by Springer-Verlag.

Morfin, F., S. Dupuis-Girod, S. Mundweiler, D. Falcon, D. Carrington, P. Sedlacek, M. Bierings, P. Cetkovsky, A. C. Kroes, M. J. van Tol, and D. Thouvenot. 2005. In vitro susceptibility of adenovirus to antiviral drugs is species-dependent. Antiviral Therapy, vol. 10, pp. 225-229, copyright by International Medical Press.

Morin, J. E., M. D. Lubeck, J. E. Barton, A. J. Conley, A. R. Davis, and P. P. Hung. 1987. Recombinant adenovirus induces antibody response to hepatitis B virus surface antigen in hamsters. Proceedings of the National Academy of Sciences USA, vol. 84, pp. 4626-4630.

Naesens, L., L. Lenaerts, G. Andrei, R. Snoeck, D. Van Beers, A. Holy, J. Balzarini, and E. De Clercq. 2005. Antiadenovirus activities of several classes of nucleoside and nucleotide analogues. Antimicrobial Agents and Chemotherapy, vol. 49, No. 3, pp. 1010-1016, copyright by American Society for Microbiology.

Quenelle, D. C., D. J. Collins, W. B. Wan, J. R. Beadle, K. Y. Hostefler, and E. R. Kern. 2004. Oral treatment of cowpox and vaccinia virus infections in mice with ether lipid esters of cidofovir. Antimicrobial Agents Chemotherapy, vol. 48, No. 2, pp. 404-412, copyright by American Society for Microbiology.

Ribaud, P., C. Scieux, F. Freymuth, F. Morinet, and E. Gluckman. 1999. Successful treatment of adenovirus disease with intravenous cidofovir in an unrelated stem-cell transplant recipient. Clinical Infectious Diseases, vol. 28, pp. 690-691, copyright by the Infectious Diseases Society of America.

Romanowski, E. G., K. A. Yates, and Y. J. Gordon. 2001. Antiviral prophylaxis with twice daily topical cidofovir protects against challenge in the adenovirus type 5/New Zealand rabbit ocular model. Antiviral Research, vol. 52, pp. 275-280, copyright by Elsevier Science B.V.

(56) References Cited

OTHER PUBLICATIONS

Schleuning, M., H. Buxbaum-Conradi, G. Jager, and H. J. Kolb. 2004. Intravenous ribavirin for eradication of respiratory syncytial virus (RSV) and adenovirus isolates from the respiratory and/or gastrointestinal tract in recipients of allogeneic hematopoietic stem cell transplants. The Hematology Journal, vol. 5, pp. 135-144, copyright by the European Hematology Association.
Thomas, M. A., J. F. Spencer, M. C. La Regina, D. Dhar, A. E. Tollefson, K. Toth, and W. S. Wold. 2006. Syrian hamster as a permissive immunocompetent animal model for the study of oncolytic adenovirus vectors. Cancer Research, vol. 66, pp. 1270-1276, copyright by American Association for Cancer Research.
Tollefson, A. E. and W. S. M. Wold. 2006. Preparation and Titration of CsC1-Banded Adenovirus Stocks in W. S. M. Wold and A. E. Tollefson (eds.), Methods in Molecular Medicine. pp. 223-235. Copyright by Humana Press, Totowa, NJ.
Toth, K., H. Djeha, B. L. Ying, A. E. Tollefson, M. Kuppuswamy, K. Doronin, P. Krajcsi, C. J. Wrighton, and W. S. M. Wold. 2004. An oncolytic adenovirus vector combining enhanced cell-to-cell spreading, mediated by the ADP cytolytic protein, with selective replication in cancer cells with deregulated Wnt signaling. Cancer Research, vol. 64, pp. 3638-3644.
Toth, K., J. F. Spencer, A. E. Tollefson, M. Kuppuswamy, K. Doronin, D. L. Lichtenstein, M. C. La Regina, G. A. Prince, and W. S. M. Wold. 2005. Cotton rat tumor model for the evaluation of oncolytic adenoviruses. Human Gene Therapy, vol. 16, pp. 139-146, copyright by Mary Ann Liebert, Inc.
Toth, K., V. Tarakanova, K. Doronin, P. Ward, M. Kuppuswamy, J. L. Locke, J. E. Dawson, H. J. Kim, and W. S. M. Wold. 2003. Radiation increases the activity of oncolytic adenovirus cancer gene therapy vectors that overexpress the ADP (E3-11.6K) protein. Cancer Gene Therapy, vol. 10, pp. 193-200, copyright by Nature Publishing Group.
Uckun, F. M., S. Pendergrass, S. Qazi, P. Samuel, and T. K. Venkatachalam. 2004. Phenyl phosphoramidate derivatives of stavudine as anti-HIV agents with potent and selective in-vitro antiviral activity against adenovirus. European Journal of Medicinal Chemistry, vol. 39, pp. 225-234, copyright by Elsevier SAS. (2003).
Walls, T., A. G. Shankar, and D. Shingadia. 2003. Adenovirus: an increasingly important pathogen in paediatric bone marrow transplant patients. The Lancet Infectious Diseases, vol. 3, pp. 79-86.
Wold, W. S. M. and M. Horwitz. 2007. Fields Virology, 5th Edition In D. M. Knipe and P. M. Howley (eds.), pp. 2395-2436, Lippincott, Williams, & Wilkins, Philadelphia. PA, in press.
Zarubaev V V et al. Effect of 6-azacytidine on the course of experimental adenoviral infection in newborn Syrian hamsters. 2007. Journal of Chemotherapy, vol. 19, No. 1, pp. 44-51, copyright by E.S.I. F.T., Florence, Italy.

Lewis A M Jr. et al. Spectrum of tumorigenic phenotypes among adenovirus type 2 transformed adenovirus type 12 transformed and SV-40 transformed Syrian hamster cells defined by host cellular immune tumor cell interactions. 1982. Cancer Research, vol. 42, No. 3, pp. 939-944.
Cook J.L. et al. Age related and thymus dependent rejection of adenovirus 2 transformed cell tumors in the Syrian hamster. 1979. Cancer Research, vol. 39, No. 9, pp. 3335-3340.
Alemany et al. Cancer selective adenoviruses. 2007. Molecular Aspects of Medicine, vol. 28, No. 1, pp. 42-58, copyright by Elsevier Ltd.
Toth, Karoly et al. Hexadecyloxypropyl-cidofovir, CMX001, prevents adenovirus-induced mortality in a permissive, immunosuppressed animal model. 2008. Proceedings of the National Academy of Sciences USA, vol. 105, No. 20, pp. 7293-7297, copyright by the National Academy of Sciences of the USA.
Wold et al., "Oncolytic adenovirus vectors that overexpress ADP for increased efficacy: evaluation in a permissive, immunocompetent, Syrian hamster model," The 14$^{th}$ International Conference on Gene Therapy of Cancer, Abstract only, Sep. 2006.
Wold et al., "Permissive immunocompetent Syrian hamster tumor model to evaluate oncolytic adenovirus vectors," The 4$^{th}$ International Conference on Oncolytic Viruses as Cancer Therapeutics, Abstract only, Mar. 2007.
Al-Hashmi et al., "Busulphan-cyclophosphamide cause endothelial injury, remodeling of resistance arteries and enhanced expression of endothelial nitric oxide synthase," PLoS ONE, 7(1):e30897, 2012.
Lapidot et al., "Immune-deficient SCID and NOD/SCID mice models as functional assays for studying normal and malignant human hematopoiesis," J Mol Med, 75(9):664-673, 1997.
Lichtenstein et al., "An acute toxicology study in INGN 007, an oncolytic adenovirus vector, in mice and permissive Syrian hamsters; comparisons with wild-type Ad5 and a replication-defective adenovirus vector," Cancer Gene Therpay, 16(8):644-654, 2009.
Malhi et al., "Cyclophosphamide disrupts hepatic sinusoidal endothelium and improves transplanted cell engraftment in rat liver," Hepatology, 36(1):112-121, 2002.
Niemeijer et al., "Chemotherapy with cyclophosphamide, vincristine and dacarbazine for malignant paraganglioma and pheochromocytoma: systematic review and meta-analysis," Clinical Endocrinology, pp. 1-10, 2014.
Ying et al., "INGN 007, an oncolytic adenovirus vector, replicates in Syrian hamsters but not mice: comparison of biodistribution studies," Cancer Gene Therapy, 16(8):625-637, 2009.
Zeng et al., "Endothelial injury, an intriguing effect of methotrexate and cyclophosphamide during hematopoietic stem cell transplantation in mice," Transplantation Proceedings, 40(8):2670-2673, 2008.

* cited by examiner

SCREENING TOOL FOR ANTIVIRAL AGENTS

CROSS-REFERENCE TO RELATED APPLICATIONS

This application is a non-provisional of and claims priority to U.S. Provisional Patent Application Ser. No. 60/939,194, filed May 21, 2007, which document is hereby incorporated by reference herein to the extent permitted by law.

BACKGROUND OF THE INVENTION

The present invention generally relates to animal models useful for screening anti-adenovirus agents. Human adenoviruses ("Ads") are a significant problem in immunosuppressed humans, especially in children undergoing allogeneic stem cell transplants. About twenty-percent of these pediatric patients develop disseminated Ad infections, and about half of these patients die. Unfortunately, there are no anti-viral drugs approved to treat these Ad infections. Cidofovir and ribavirin are used in some cases, but it is not known whether they are effective because they have not been studied in a systematic controlled manner. Anti-Ad drugs have not been studied in vivo because there is no animal model for replicating human Ads. This is because Ads have been considered to be highly species-specific. Therefore, it would be beneficial to provide a suitable animal model of systemic disease.

Ads have an icosahedral protein capsid that encloses a linear duplex DNA genome of 36 kpb and about 34 genes. Ads enter cells via receptor-mediated endocytosis and express their genes in the cell nucleus. Genes are expressed in two phases (1) an "early" phase, which precedes viral DNA replication, and (2) a "late" phase, which follows the initiation of viral DNA replication. Early gene products convert the cell into a factory for viral DNA replication, and late gene products are primarily components of the virion. Virus assembles in the cell nucleus by about one day post infection, and after about 2-3 days the cells begin to lyse and release infectious virus particles.

Human Ads are divided into six species, A, B, C, D, E, and F. There are 51 known human serotypes in the six species of human Ads: Species A (Ad12, 18, 31), Species B (Ad3, 7, 11, 14, 16, 34, 35, 50), Species C (Ad1, 2, 5, 6), Species D (Ad8-10, 13, 15, 17, 19, 20, 22-30, 32, 33, 36-39, 42-49, 51), Species E (Ad4), and Species F (Ad40 and 41). Species B can be further divided into Species B1 (Ad3, 7, 11, 21, 50) and B2 (Ad11, 14, 34, 35). A serotype is defined based on neutralization with specific antisera.

The different Ads cause a wide variety of common and sporadic infections and there is not a strict one-to-one relationship between the serotype and disease (see Table 1 below). However, clear generalizations can be made. Ads in Species C, B1, and E cause respiratory tract infections, with Species C and the lower B1 serotypes (Ad3 and Ad7) predominating in infants and young children and Ad7 and Ad4 (Species E) causing acute respiratory disease (ARD) in military recruits. Species C and Ad3 cause conjunctivitis and pharyngealconjunctival fever. Species F (Ad40 and Ad41) causes gasteroentitis, especially in children. Species B2 infects the kidney and urinary tract (causing hemorrhagic cystitis). Species D, especially Ad8, 19, and 37, cause epidemic keratoconjunctivitis (EKC) throughout the world. For the most part, the molecular basis for these differences in pathogenicity is not understood. Ads not only cause disease as described above and as illustrated in Table 1 herein, Ads are also a significant problem in immunocompromised patients, as described below.

Ads have been isolated from immunocompromised hosts, in particular transplant patients, and have contributed to their morbidity and mortality. Pediatric allogeneic stem cell transplant patients under sever immunosuppression are particularly at risk. Roughly twenty-percent of these patients develop disseminated adenoviremia, usually of Species C serotypes but also of other serotypes as well.

The key factor associated with Ad disease is low T cell counts at the initial time of Ad detection in the blood. These low T cell counts are often the result of T cell depletion using agents such as alemtuzumab (a monoclonal antibody against CD52) in vitro and in vivo, selection of $CD4^+$ stem cells in vitro, and continued immunosuppression following the transplant. The virus often appears in the blood about three weeks before the onset of symptoms, and virus DNA levels in the blood of greater than $10^6$ to $10^7$ copies/ml pose an increased risk for fatal outcome. Fatalities due to Ad are caused by hepatitis, pneumonia, and enteritis. Pediatric patients are more at risk for Ad, including disseminated disease and death, possibly because they are more commonly infected with the lower serotypes, especially Species C, and because their antibody and T cell response to Ad are not as developed as in adults who have species cross-reactive T cells. In pediatric transplant patients, the most common serotypes seen are in Species C, and these types can cause fatal disseminated disease. The use of real-time quantitative PCR (qPCR) is recommended to monitor Ad in the blood at successive times following transplantation, especially in T cell-depleted grafts, looking for an increase in viral load and, if possible, withdrawal of immunosupression. Another situation in which Ad is linked to immunosuppression is acquired immunodeficiency syndrome (AIDS). Twelve-percent of patients with AIDS have been reported to have Species B Ads in their urine.

TABLE 1

| Disease | Individuals most at risk | Principal serotypes |
|---|---|---|
| Acute febrile pharyngitis | Infants, young children | 1-3, 5-7 |
| Pharyngoconjunctival fever | School-aged children | 3, 7, 14 |
| Acute respiratory disease | Military recruits | 3, 4, 7, 14, 21 |
| Pneumonia | Infants, young children | 1-3, 7 |
| Pneumonia | Military recruits | 4, 7 |
| Epidemic keratoconjunctivitis | Any age group | 8, 11, 19, 37 |
| Pertussis-like syndrome | Infants, young children | 5 |
| Acute hemorrhagic cystitis | Young children | 11, 21 |
| Gastroenteritis | Infants, young children | 40, 41 |
| Meningoencephalitis | Children and immunocompromised hosts | 7, 12, 32 |
| Hepatitis | Infants and children with liver transplants | 1, 2, 5 |
| Myocarditis | Children | ? |

TABLE 1-continued

| Disease | Individuals most at risk | Principal serotypes |
|---|---|---|
| Persistence: | -Bone marrow transplant recipients; patients with acquired immunodeficiency or other immunosuppression syndromes | |
| In urinary tract | | 34-35 |
| In colon | | 42-49 |

Modified from refs. (164, 259), with permission.

With the emerging appreciation that Ads are a serious problem in immunosuppressed patients, there is strong interest in developing anti-Ad drugs. A class of drugs known as acyclic nucleoside phosphonates is effective against many viruses including Ads. One member of this class, (S)-9-[3-hydroxy-2-(phosphonomethyloxy)propyl] cytosine, known as cidofovir, has been studied extensively in Ad infections. Cidofovir is an analogue of 2',3'-dideoxycytosine. Cidofovir is a monophosphate, and it is converted to the di- and triphosphate forms by cellular enzymes. These compounds have much higher affinity for viral DNA polymerases than for cellular DNA polymerases, thereby providing specificity for virus-infected cells. They act as inhibitors of the polymerase, and the triphosphate is a substrate for the polymerase, acting as a DNA synthesis chain terminators. Cidifivor is approved for treatment via the intravenous route for cytomegalovirus retinitis in AIDS patients.

Cidofovir is a potent, nontoxic inhibitor of Ad replication in cell culture, including serotypes 1, 2, 5, and 8. As shown in FIG. 1, cidofovir inhibits the replication of our Ad5-based vector named VRX-007. In a recent study, cidofovir inhibited replication in HEp-2 cells of serotypes from Species A, B, D, E, and F. Only Species C was inhibited by ribavirin. A549 cells were mock-infected or infected with 10 or 0.1 plaque-forming units (PFU)/cell of VRX-007. Concomitantly, cidofovir was added to the medium at the indicated concentrations. The cells were stained with crystal violet dye at seven days post infection. Cidofovir has shown some efficacy in the rabbit and cotton rat models of ocular models of Ad5 infection.

A large multi-center trial was initiated in the United States to evaluate cidofovir against Ad ocular infections in humans. Significant efficacy was observed, but the trial was discontinued because of a narrow efficacy/toxicity ratio. Two other known clinical trials have been conducted for cidofovir treatment of EKC. In the first trial, no efficacy was seen using 0.2% cidofovir plus 1% cyclosporine. In the second trial, 1% cidofovir plus 1% cyclosporine lowered the frequency of severe corneal opacities but caused local toxicity.

Cidofovir has also been examined in a number of retrospective studies as well as in case reports, alone or sometimes in combination with ribavirin, to treat Ad in immunosuppressed patients. However, there have not been controlled clinical trials for systemic use of these drugs to treat Ad, and the drugs have not been licensed for this use. Cidofovir showed some efficacy against Ad in patients immunosuppressed because of stem cell and bone marrow transplants. Cidofovir was effective against Ad-associated hemorrhagic cystitis and renal dysfunction in bone marrow transplant patients. In a known prospective study of eight pediatric stem cell transplant patients, cidofovir treatment seemed to provide long term suppression of Ad without dose-limiting nephrotoxicity. In a recent known prospective study in which Ad was detected in 26 of 155 pediatric stem cell transplant patients, ribavirin was used when Ad was first detected and cidofovir was used in patients with persistent viremia. Although not curative, the antiviral therapy appeared to control the Ad infection. Cidofovir seemed to resolve disseminated Ad in a pediatric liver transplant patient and Ad7 in a B cell lymphoma adult patient with meningoencepahlitis. Although these various studies are somewhat encouraging, one major problem with the systemic use of cidofovir is nephrotoxicity caused by accumulation of the drug in renal proximal tubules.

Because of the presence of the phosphonate group on cidofovir, the drug shows poor oral bioavailability. However, a new series of bioavailable ether lipid-ester prodrugs of cidofovir and a related acyclic nucleoside phosphonate has been developed that were reported to be 15-2,500-fold more effective in inhibiting Ad in cell culture.

The following references that are referred throughout this disclosure are hereby incorporated herein in their entirety to the extent permitted by laws. These references merely serve to support the invention and to provide background and context. Applicant reserves the right to challenge the veracity of any statements therein made.

Aldern, K. A., S. L. Ciesla, K. L. Winegarden, and K. Y. Hostetler. 2003. Increased antiviral activity of 1-O-hexadecyloxypropyl-[2-(14)C]cidofovir in MRC-5 human lung fibroblasts is explained by unique cellular uptake and metabolism. Mol. Pharmacol. 63:678-681.

Beadle, J. R., C. Hartline, K. A. Aldern, N. Rodriguez, E. Harden, E. R. Kern, and K. Y. Hostefler. 2002. Alkoxyalkyl esters of cidofovir and cyclic cidofovir exhibit multiple-log enhancement of antiviral activity against cytomegalovirus and herpesvirus replication in vitro. Antimicrob. Agents Chemother. 46: 2381-2386.

Bidanset, D. J., J. R. Beadle, W. B. Wan, K. Y. Hostetler, and E. R. Kern. 2004. Oral activity of ether lipid ester prodrugs of cidofovir against experimental human cytomegalovirus infection. J. Infect. Dis. 190:499-503.

Bordigoni, P., A. S. Carret, V. Venard, F. Witz, and A. Le Faou. 2001. Treatment of adenovirus infections in patients undergoing al logeneic hematopoietic stem cell transplantation. Clin. Infect. Dis. 32:1290-1297.

Buller, R. M., G. Owens, J. Schriewer, L. Melman, J. R. Beadle, and K. Y. Hostetler. 2004. Efficacy of oral active ether lipid analogs of cidofovir in a lethal mousepox model. Virology 318:474-481.

Carter, B. A., S. J. Karpen, R. E. Quiros-Tejeira, I. F. Chang, B. S. Clark, G. J. Demmler, H. E. Heslop, J. D. Scott, P. Seu, and J. A. Goss. 2002. Intravenous Cidofovir therapy for disseminated adenovirus in a pediatric liver transplant recipient. Transplantation 74:1050-1052.

Ciesla, L. L., J. Trahan, W. B. Wan, J. R. Beadle, K. A. Aldem, G. R. Painter, and K. Y. Hostetler. 2003. Exterification of cidofovir with alkoxyalkanola increases oral bioavailability and diminishes drug accumulation in kidney. Antiviral Res. 59:163-171.

De Clercq, E. and A. Holy. 2005. Acyclic nucleoside phosphonates: a key class of antiviral drugs. Nat. Rev. Drug Discov. 4:928-940.

Doronin, K., M. Kuppuswamy, K. Toth, A. E. Tollefson, P. Krajcsi, V. Krougliak, and W. S. M. Wold. 2001. Tissue-specific, tumor-selective, replication-competent adenovirus vector for cancer gene therapy. J. Virol. 75:3314-3324.

Doronin, K., K. Toth, M. Kuppuswamy, P. Krajcsi, A. E. Tollefson, and W. S. M. Wold. 2003. Overexpression of the ADP (~3-11.6K) protein increases cell lysis and spread of adenovims. Virology 305:378-387.

Doronin, K., K. Toth, M. Kuppuswamy, P. Ward, A. E. Tollefson, and W. S. M. Wold. 2000. Tumor-specific, replication-competent adenovirus vectors overexpressing the Adenovirus Death Protein. J. Virol. 74:6147-6155.

Fanourgiakis, P., A. Georgala, M. Vekemans, A. Triffet, J. M. De Bruyn, V. Duchateau, P. Martiat, E. De Clercq, R. Snoeck, E. Wollants, A. Rector, M. Van Ranst, and M. Aoun. 2005. Intravesical instillation of cidofovir in the treatment of hemorrhagic cystitis caused by adenovirus type 11 in a bone marrow transplant recipient. Clin. Infect. Dis. 40:199-201.

Fianchi, L., A. Scardocci, P. Cattani, T. Tartaglione, and L. Pagano. 2003. Adenovirus meningoencephalitis in a patient with large B-cell lymphoma. Ann. Hematol. 82:313-315.

Habib, N. A., R. Mitry, P. Seth, M. Kuppuswamy, K. Doronin, K. Toth, P. Krajcsi, A. E. Tollefson, and W. S. M. Wold. 2002. Adenovirus replication-competent vectors (KD 1, KD3) complement the cytotoxicity and transgene expression from replication-defective vectors (AdGFP, Ad-Luc). Cancer Gene Ther. 9:651-654.

Hartline, C. B., K. M. Gustin, W. B. Wan, S. L. Ciesla, J. R. Beadle, K. Y. Hostetler, and E. R. Kern. 2005. Ether lipid-ester prodrugs of acyclic nucleoside phosphonates: activity against adenovirus replication in vitro. J. Infect. Dis. 191: 396-399.

Hatakeyama, N., N. Suzuki, T. Kudoh, T. Hori, N. Mizue, and H. Tsutsumi. 2003. Successful cidofovir treatment of adenovirus-associated hemorrhagic cystitis and renal dysfunction after allogenic bone marrow transplant. Pediatr. Infect. Dis. J. 22:928-929.

Hillenkamp, J., T. Reinhard, R. S. Ross, D. Bohringer, O. Cartsburg, M. Roggendorf, E. De Clercq, E. Godehardt, and R. Sundmacher. 2001. Topical treatment of acute adenoviral keratoconjunctivitis with 0.2% cidofovir and 1% cyclosporine: a controlled clinical pilot study. Arch. Opthalmol. 119:1487-1491.

Hillenkamp, J., T. Reinhard, R. S. Ross, D. Bohringer, O. Cartsburg, M. Roggendorf, E. De Clercq, E. Godehardt, and R. Sundmacher. 2002. The effects of cidofovir 1% with and without cyclospodn a 1% as a topical treatment of acute adenoviral keratoconjunctivitis: a controlled clinical pilot study. Opthalmology 109: 845-850.

Hjorth, R. N., G. M. Bonde, W. A. Pierzchala, S. K. Vernon, F. P. Wiener, M. H. Levner, M. D. Lubeck, and P. P. Hung. 1988. A new hamster model for adenoviral vaccination. Arch. Virol. 100:279-283.

Hoffman, J. A., A. J. Shah, L. A. Ross, and N. Kapoor. 2001. Adenoviral infections and a prospective trial of cidofovir in pediatric hematopoietic stem cell transplantation. Biol. Blood Marrow Transplant. 7:388-394.

Hostetler, K. Y., J. R. Beadle, J. Trahan, K. A. Aldern, G. Owens, J. Schriewer, L. Melman, and R. M. Buller. 2006. Oral 1-O-octadecyl-2-O-benzyl-sn-glycero-3-cidofovir targets the lung and is effective against a lethal respiratory challenge with ectromelia virus in mice. Antiviral Res.

Kampmann, B., D. Cubitt, T. Walls, P. Naik, M. Depala, S. Samarasinghe, D. Robson, A. Hassan, K. Rao, H. Gaspar, G. Davies, A. Jones, C. Cale, K. Gilmour, M. Real, M. Foo, N. Bennett-Rees, A. Hewitt, P. Ammolia, and P. Veys. 2005. Improved outcome for children with disseminated adenoviral infection following allogeneic stem cell transplantation. Br. J. Haematol. 130:595-603.

Kaneko, H., T. Fujiwara, S. Mori, and S. Shigeta. 2000. Evaluation of antiviral agents for adenovirus using the MTI method in vitro. Nippon Ganka Gakkai Zasshi 104:786-791.

Kaneko, H., S. Mori, O, Suzuki, T. Iida, S. Shigeta, M. Abe, S. Ohno, K. Aoki, and T. Suzutani. 2004. The cotton rat model for adenovirus ocular infection: antiviral activity of cidofovir. Antiviral Res. 61:63-66.

Kern, E. R., D. J. Collins, W. B. Wan, J. R. Beadle, K. Y. Hostetler, and D. C. Quenelle. 2004. Oral treatment of murine cytomegalovirus infections with ether lipid esters of cidofovir. Antimicrob. Agents Chemother. 48:3516-3522.

Kinchington, P. R., E. G. Romanowski, and G. Y. Jerold. 2005. Prospects for adenovirus antivirals. J. Antimicrob. Chemother. 55:424-429.

Kojaoghlianian, T., P. Flomenberg, and M. S. Horwitz. 2003. The impact of adenovirus infection on the immunocompromised host. Rev. Med. Virol. 13:155-171.

Kuhl, U., M. Pauschinger, P. L. Schwimmbeck, B. Seeberg, C. Lober, M. Noutsias, W. Poller, and H. P. Schultheiss. 2003. Interferon-beta treatment eliminates cardiotropic viruses and improves left ventricular function in patients with myocardial persistence of viral genomes and left ventricular dysfunction. Circulation 107:2793-2798.

Kuppuswamy, M., J. F. Spencer, K. Doronin, A. E. Tollefson, W. S. Wold, and K. Toth. 2005. Oncolytic adenovirus that overproduces ADP and replicates selectively in tumors due to hTERT promoter-regulated E4 gene expression. Gene Ther. 12:1608-1617.

Leen, A. M., C. M. Bollard, G. D. Myers, and C. M. Rooney. 2006. Adenoviral infections in hematopoietic stem cell transplantation. Biol. Blood Marrow Transplant. 12:243-251.

Legrand, F., D. Berrebi, N. Houhou, F. Freymuth, A. Faye, M. Duval, J. F. Mougenot, M. Peuchmaur, and E. Vilmer. 2001. Early diagnosis of adenovirus infection and treatment with cidofovir after bone marrow transplantation in children. Bone Marrow Transplant. 27: 621-626.

Lichtenstein, D. L., K. Toth, K. Doronin, Tollefson A. E., and W. S. M. Wold. 2004. Functions and mechanisms of action of the adenovirus E3 proteins. Int. Rev. Immunol. 23:75-111.

Ljungman, P. 2004. Treatment of adenovirus infections in the immunocompromised host. Eur. J. Clin. Microbiol. Infect. Dis. 23:583-588.

Morfin, F., S. Dupuis-Girod, S. Mundweiler, D. Falcon, D. Carrington, P. Sedlacek, M. Bierings, P. Cetkovsky, A. C. Kroes, M. J. van Tol, and D. Thouvenot. 2005. In vitro susceptibility of adenovirus to antiviral drugs is species-dependent. Antivir. Ther. 10:225-229.

Morin, J. E., M. D. Lubeck, J. E. Barton, A. J. Conley, A. R. Davis, and P. P. Hung. 1987. Recombinant adenovirus induces antibody response to hepatitis B virus surface antigen in hamsters. Proc. Natl. Acad. Sci. USA 84:4626-4630.

Naesens, L., L. Lenaerts, G. Andrei, R. Snoeck, D. Van Beers, A. Holy, J. Balzarini, and E. De Clercq. 2005. Antiadenovirus activities of several classes of nucleoside and nucleotide analogues. Antimicrob. Agents Chemother. 49:1010-1016.

Quenelle, D. C., D. J. Collins, W. B. Wan, J. R. Beadle, K. Y. Hostefler, and E. R. Kern. 2004. Oral treatment of cowpox and vaccinia virus infections in mice with ether lipid esters of cidofovir. Antimicrob. Agents Chemother. 48:404-412.

Ribaud, P., C. Scieux, F. Freymuth, F. Morinet, and E. Gluckman. 1999. Successful treatment of adenovirus disease with intravenous cidofovir in an unrelated stem-cell transplant recipient. Clin. Infect. Dis. 28:690-691.

Romanowski, E. G., K. A. Yates, and Y. J. Gordon. 2001. Antiviral prophylaxis with twice daily topical cidofovir protects against challenge in the adenovirus type 5/New Zealand rabbit ocular model. Antiviral Res. 52:275-280.

Schleuning, M., H. Buxbaum-Conradi, G. Jager, and H. J. Kolb. 2004. Intravenous ribavirin for eradication of respiratory syncytial virus (RSV) and adenovirus isolates from the respiratory and/or gastrointestinal tract in recipients of allogeneic hematopoietic stem cell transplants. Hematol. J. 5:135-144.

Thomas, M. A., J. F. Spencer, M. C. La Regina, D. Dhar, A. E. Tollefson, K. Toth, and W. S. Wold. 2006. Syrian hamster as a permissive immunocompetent animal model for the study of oncolytic adenovirus vectors. Cancer Res. 66:1270-1276.

Tollefson, A. E. and W. S. M. Wold. 2006. Preparation and Titration of CsC1-Banded Adenovirus Stocks in W. S. M. Wold and A. E. Tollefson (eds.), Methods in Molecular Medicine. Humana Press, Totowa, N.J.

Toth, K., H. Djeha, B. L. Ying, A. E. Tollefson, M. Kuppuswamy, K. Doronin, P. Krajcsi, C. J. Wrighton, and W. S. M. Wold. 2004. An oncolytic adenovirus vector combining enhanced cell-to-cell spreading, mediated by the ADP cytolytic protein, with selective replication in cancer cells with deregulated Wnt signaling. Cancer Res. 64:3638-3644.

Toth, K., J. F. Spencer, A. E. Tollefson, M. Kuppuswamy, K. Doronin, D. L. Lichtenstein, M. C. La Regina, G. A. Prince, and W. S. M. Wold. 2005. Cotton rat tumor model for the evaluation of oncolytic adenoviruses. Hum. Gene Ther. 16:139-146.

Toth, K., V. Tarakanova, K. Doronin, P. Ward, M. Kuppuswamy, J. L. Locke, J. E. Dawson, H. J. Kim, and W. S. M. Wold. 2003. Radiation increases the activity of oncolytic adenovirus cancer gene therapy vectors that overexpress the ADP (E3-11.6K) protein. Cancer Gene Ther. 10:193-200.

Uchio, E. 2005. New medical treatment for viral conjunctivitis. Nippon Ganka Gakkai Zasshi 109:962-984.

Uckun, F. M., S. Pendergrass, S. Qazi, P. Samuel, and T. K. Venkatachalam. 2004. Phenyl phosphoramidate derivatives of stavudine as anti-HIV agents with potent and selective in-vitro antiviral activity against adenovirus. Eur. J. Med. Chem. 39:225-234.

Walls, T., A. G. Shankar, and D. Shingadia. 2003. Adenovirus: an increasingly important pathogen in paediatric bone marrow transplant patients. Lancet Infect. Dis. 3:79-86.

Wold, W. S. M. and M. Horwitz. 2007. Fields Virology, 5th Edition In D. M. Knipe and P. M. Howley (eds.), Lippincott, Williams, & Wilkins, Philadelphia. Pa., in press.

SUMMARY OF THE INVENTION

The present invention is directed to animal models useful for screening anti-adenovirus agents. In particular, a method for screening anti-adenovirus agents including the steps of reducing the activation of the immune system of a small mammal, administering a human adenovirus vector to the small mammal, monitoring the tumor cells that grow or shrink in the small mammal, and analyzing infectious virus units and the organs of the small mammal. Specifically, the immune system of the small mammal is suppressed using cyclophosphamide. The small mammal may be, but is not limited to, one of the following: mice, rabbits, cotton rats, hamsters, rats, and other small rodents.

An object of the invention is the use of the immunosuppressed hamster as a model with which to evaluate drugs to treat Ad infections in immunocompromised hosts. In a particular non-limiting example, the effectiveness of the lipid-ester prodrug, HDP-CDV, is demonstrated in inhibiting the replication of the Ad5 in an immunosupressed Syrian hamster model. In one embodiment, CP-immunosuppressed hamsters are deployed as a model to evaluate the efficacy and toxicology of anti-Ad drugs on disseminated Ad infections in immunocompromised patients.

Other and further objects of the invention, together with the features of novelty appurtenant thereto, will appear in the course of the following description.

BRIEF DESCRIPTION OF THE SEVERAL VIEWS OF THE DRAWING

In the accompanying drawings, which form a part of the specification and are to be read in conjunction therewith in which like reference numerals are used to indicate like or similar parts of the various views.

DETAILED DESCRIPTION OF THE INVENTION

The immunosuppression of Syrian hamsters using cyclophosphamide CP allows for remarkably high and prolonged levels of Ads replication in the tumors as well as in the liver and probably in other tissues.

The use of the Syrian hamster as a model to study the efficacy, biodistribution, and safety of replication-competent (oncolytic) Ad vectors for cancer gene therapy is provided. It had been shown previously that human Ad serotype 5 (Ad5) and Ad5-based vectors replicate surprisingly well in hamster tumors growing in hamsters following intratumoral injection of the viruses. These viruses also replicate well in the hamster livers, lungs, and other organs following intravenous injection (see Morin et al., PNAS 1987; 84; 4626-4630, Wold et al., U.S. Patent Pub. No. US2005/0201936, and Toth et al., Hexadecyloxypropyl-cidofovir, CMX001, prevents adenovirus induced mortality in a permissive, immunosuppressed animal model, PNAS May 20, 2008; vol. 105, no. 20, 7293-7297 which are herein incorporated by reference). Of great interest, immunosuppression of the hamsters using CP leads to much higher levels of replication of the viruses. Replication continues at high levels in tumors and livers for at least 42 days (the end of the experiment) following administration of the virus.

Throughout the instant disclosure, Applicant references the Ad vector VRX-007. VRX-007 is exactly like Ad5 except it has a deletion in the "E3 transcription unit" which removes the E3 6.7K, gp19K, RIDα, RIDβ, and 14.7K genes, and it overexpresses an E3 protein named ADP which is coded by the adp gene. These various E3-derived proteins are thought to protect Ad-infected cells from destruction by the host immune system. It is not known if these proteins exert their function in hamsters. Importantly the deletion of these genes does not affect virus replication in cell culture or in hamsters. Therefore, the data related to VRX-007 are directly applicable to Ad5.

Figure 1:
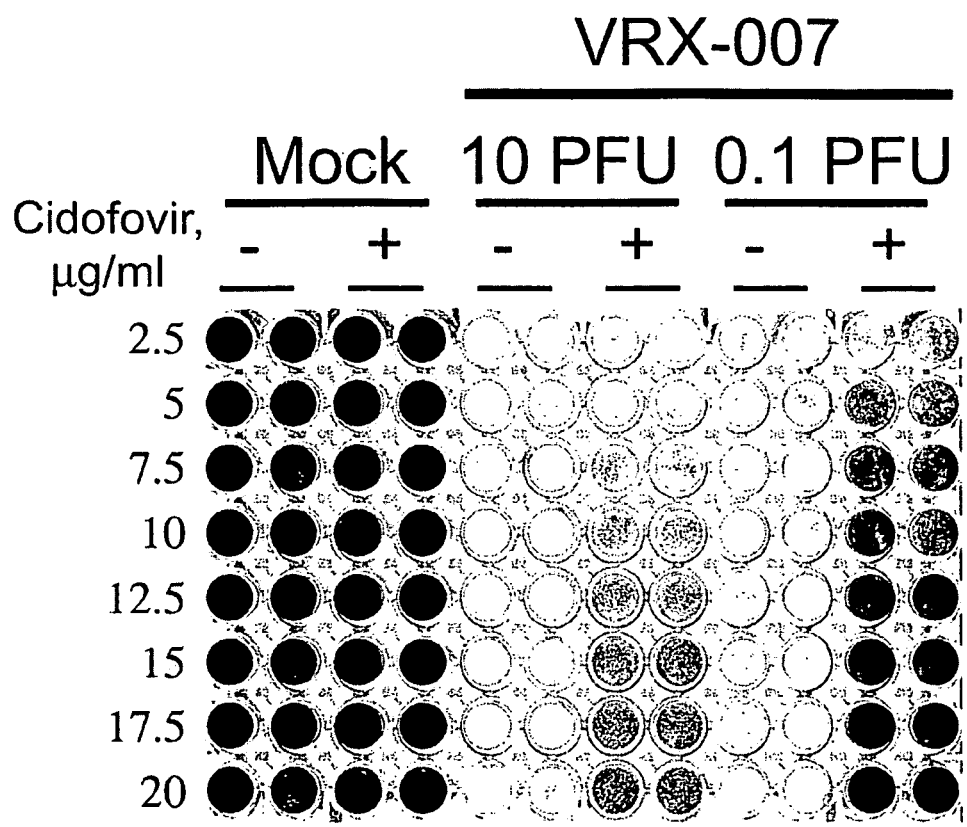
FIG. 1 (prior art) is a representation of how cidofovir inhibits the replication of VRX-007 in A549 cells.
Figure 2:
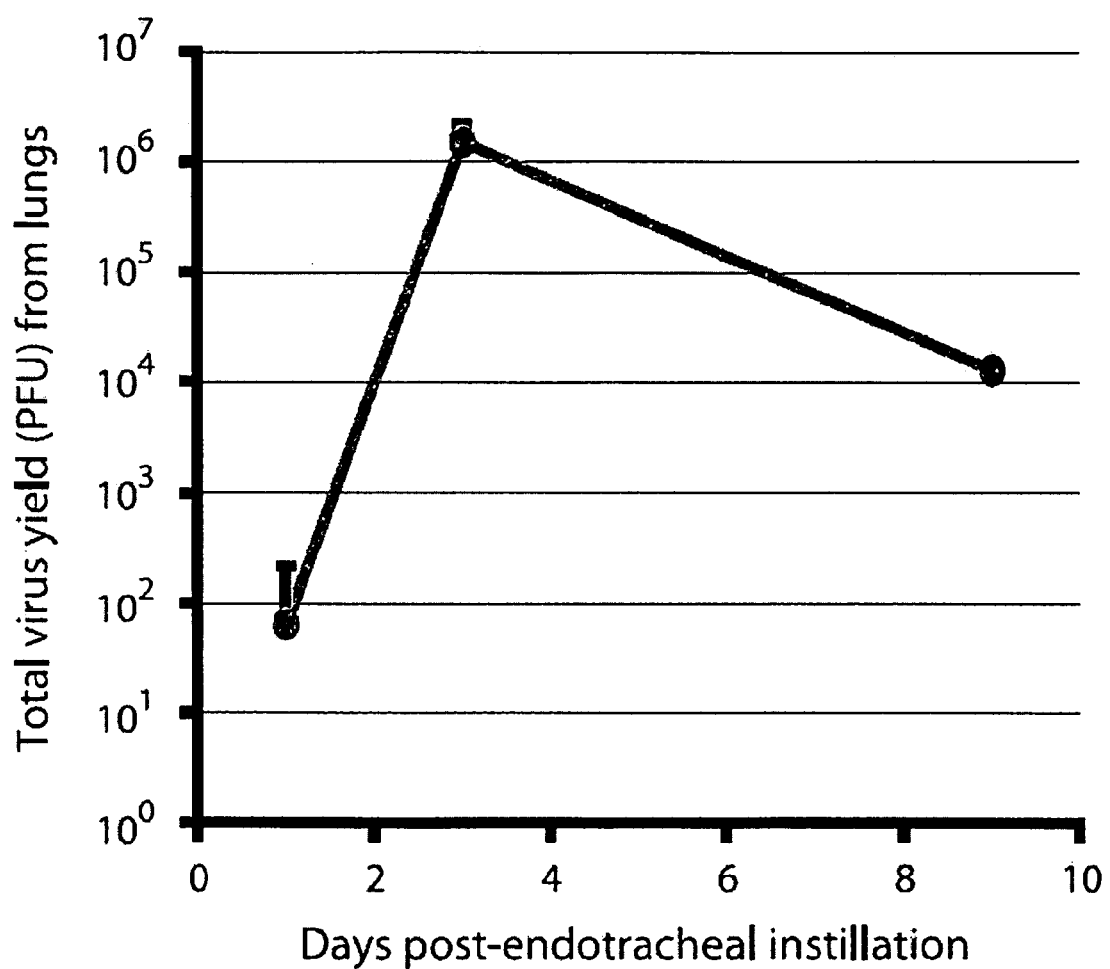
FIG. 2 is a graphical representation of Ad5 replication in the lungs of Syrian hamsters.

Ads are currently being studied widely as vectors for gene therapy. A series of oncolytic Ad vectors for cancer gene therapy in humans is known. The vectors are genetically-engineered versions of Ad5. One current problem facing researchers in the oncolytic Ad field is a proper animal model for these vectors. Human Ads are quite species-specific, and in particular they replicate very poorly in non-immunosuppressed mice and rats. However, the use of an immunosuppressed small mammal such as a hamster, mice, cotton rat, rat, or rabbit, as a model to evaluate the anti-tumor efficacy, safety, biodistribution, and pharmacokinetics of the vectors is a new approach. A four log increase of Ad5 titer in the lungs when inoculated intranasally or intratracheally has been demonstrated. FIG. 2 illustrates the representation of Ad5 replication in the lungs of Syrian hamsters. $10^7$ plaque forming units (PFU) of Ad5 were administered to hamsters by endotracheal instillation. At the days postinstillation shown in the figures, the hamsters were euthanized. The lungs were collected and suspended in buffer. Virus was extracted and titered by plaque assay on human cells. The mean total PFU recovered is plotted against the days post instillation. There were two hamsters at the 1 day time point, 2 at 3 days, and 1 at 9 days.

Further, it is shown that Ad5 and VRX-007 replicate very well in three different hamster cancer cell lines. The yield (burst size) of VRX-007 and Ad5 in these hamster cancer cell lines is only about one log less than in human A549 cells, the most permissive human cancer cell line known. These cells form subcutaneous tumors when injected into the hind flanks of hamsters. Injection of Ad5 or VRX-007 into the tumors results in replication of Ad5 and VRX-007 in the tumors and consequent suppression of the growth of the tumors. A humoral response develops against the viruses that may be shown by virus neutralization, western blot, or indirect immunofluorescence.

As previously demonstrated, when oncolytic Ad vectors were injected into tumors in hamsters, the vector replicated in the tumor, killing the tumor cells and spreading from cell-to-cell in the tumor. Further, a strong antibody and presumably CTL response developed against the vector following intratumoral injection of the vector. If the immune response is blunted, then there may be an increase in the efficacy of the vector.

Figure 3:
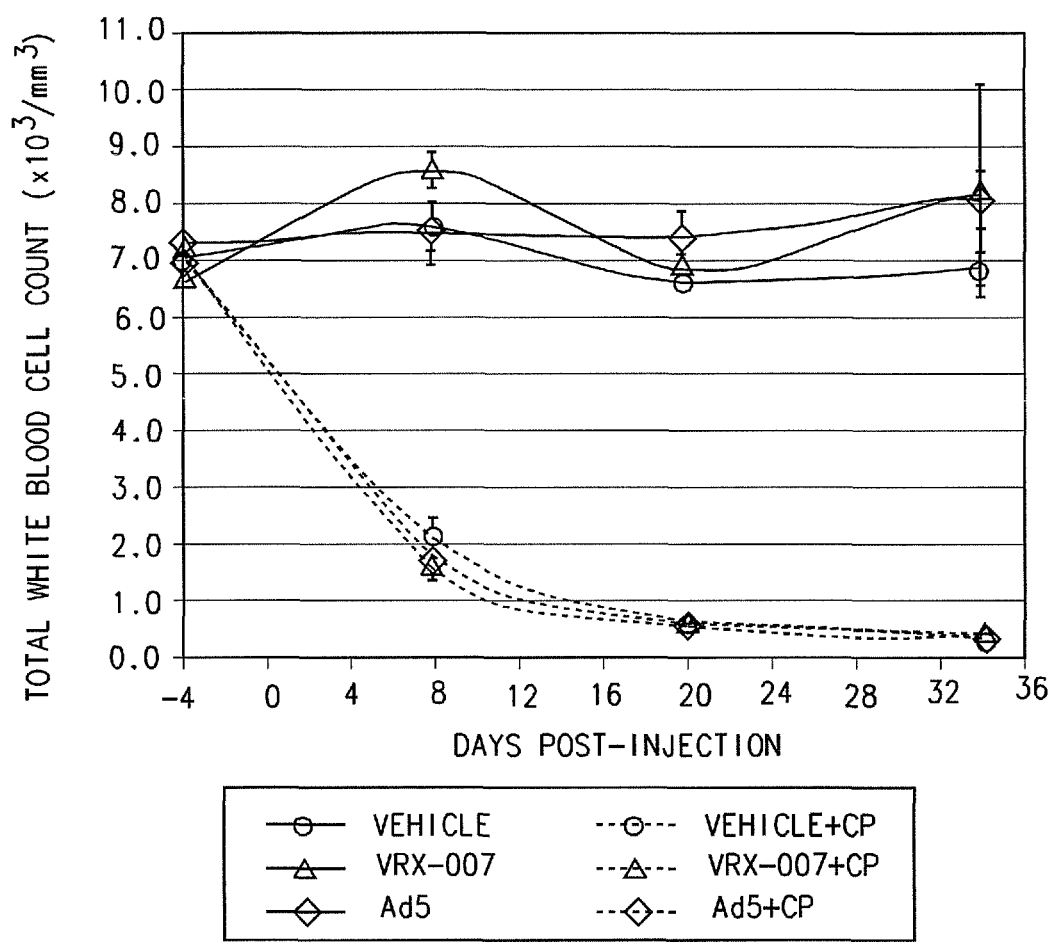
FIG. 3 is a graphical representation of white blood cell (WBC) counts that are suppressed by CP in hamsters bearing HaK tumors injected with VRX-007, Ad5, or vehicle.
Figure 4:
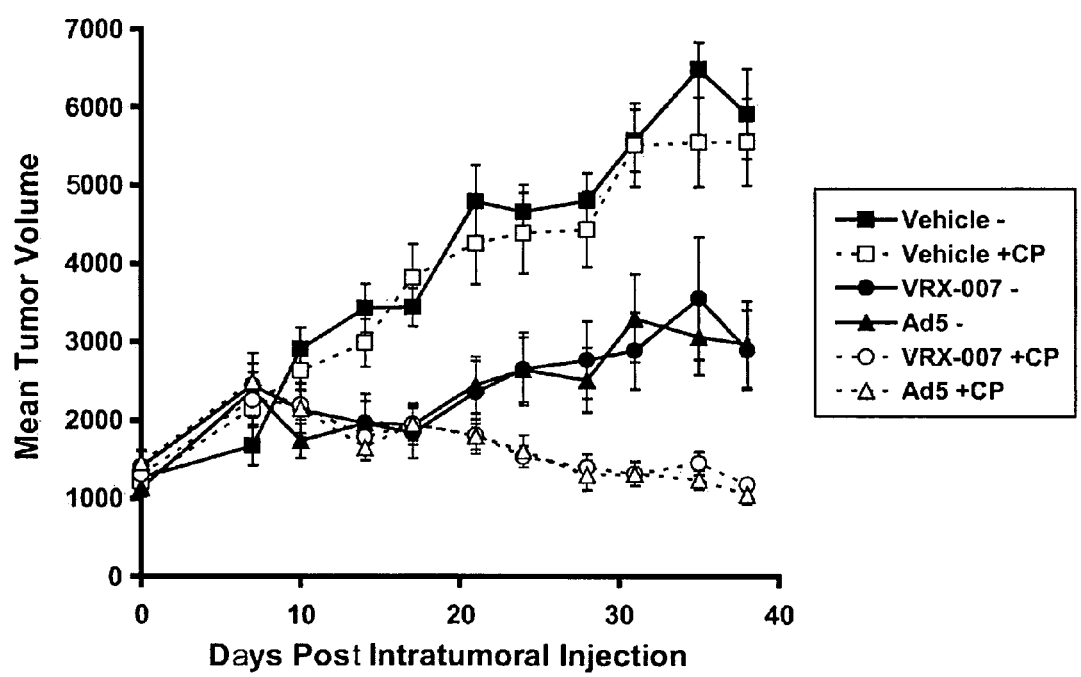
FIG. 4 is a graphical representation of the growth of tumors and illustrating that the combination of vector plus CP is more efficacious in suppressing HaK tumors in hamsters than vector alone.
Figure 5:
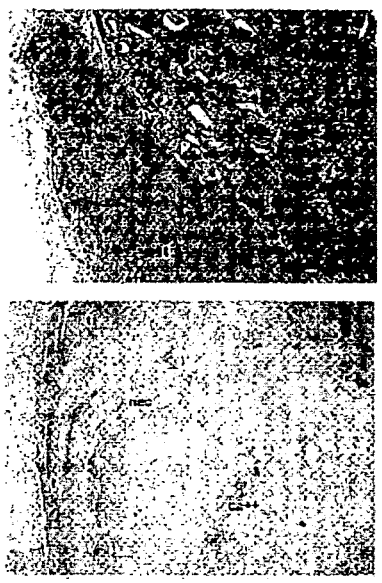
FIG. 5 is Histopathology of H&E stained tumor sections. The figure illustrates the dramatic replication of VRX-007 in the tumors of CP-treated hamsters and the consequent destruction of the tumor.

In an illustrative example, a tumor experiment in hamsters immunosuppressed with cyclophosphamide (CP) was conducted. Hamsters with very large (about 1.1 ml mean) established tumors (formed by the hamster renal cancer cell line named HaK) were treated with CP on day 1, then starting on day 4 the tumors were injected with VRX-007, Ad5, or buffer. CP was administered twice weekly throughout the study. Hamsters were bled at 1, 12, 24, and 36 days, and the blood was analyzed for different cell types, liver enzymes, and standard serum chemistry parameters (total bilirubin, creatinine, blood urea nitrogen, glucose, inorganic phosphate, calcium, total protein, albumin). As shown in FIG. 3, the total white blood cell (WBC) count dropped to very low levels by day 12 and declined further at the later time points. Similar results were obtained with neutrophils, lymphocytes, monocytes, and eosinophils (not shown). Established large, about 1.1 ml, subcutaneous HaK tumors were injected intratumorally (6 injections, $1\times10^{10}$ PFU each) with VRX-007, wild-type Ad5, or vehicle (saline only). For each of these treatments, one group was immunosuppressed with CP and one group remained immunocompetent. Tumor volumes were measured with digital calipers twice per week. The WBC counts are shown in FIG. 3. These data indicate that the animals were severely immunosuppressed by CP. FIG. 4 illustrates that tumor suppression was significantly greater in the CP-treated groups than the virus-injected groups not treated with CP. FIG. 5 illustrates that when these tumors were examined histologically, the vector-injected tumors were nearly completely necrotic and had extensive areas of calcification, with only a very small rim of proliferating tumor cells on the edge of the tumor. The tumors are from the 42 day time point. In FIG. 5, only a portion of the tumors is shown with t=tumor, nec=necrosis, and Ca++=calcification. The left panel shows the vehicle tumor and there were viable tumor cells throughout the tumor. On the left, the tumor has engulfed benign fat cells (the white cells). The right panel shows the VRX-007-injected tumor and nearly the entire tumor was necrotic and there were extensive areas of calcification. At the left is fibrous tissue and then a collagen pseudocapsule. Then there is a thin layer of viable tumor cells. Tumors from the VRX-007-injected non-CP hamsters had necrosis but there were more tumor cells on the periphery of the tumor. Although CP is used in chemotherapy of cancer, the CP did not affect growth of the buffer-injected tumors, as shown in FIG. 4, indicating that the CP augmented the oncolytic effect of the vector.

The experiment was terminated after 42 days. The hemoglobin levels averaged 15.95 g/dl at the start of the experiment; by the end of the experiment they had gradually declined to an average of 6.95 g/dl in the CP-treated hamsters. In human females, hemoglobin of <12 g/dl is considered to be anemic (the hamsters were females); −4 g/dl can be tolerated. The red blood cells (RBC) declined from $8.39 \times 10^6/mm^3$ at the start of the experiment to $3.96 \times 10^6$ $mm^3$ in the CP-treated hamsters. The hemoglobin and RBC counts were unchanged in the hamsters not treated with CP.

Figure 6:
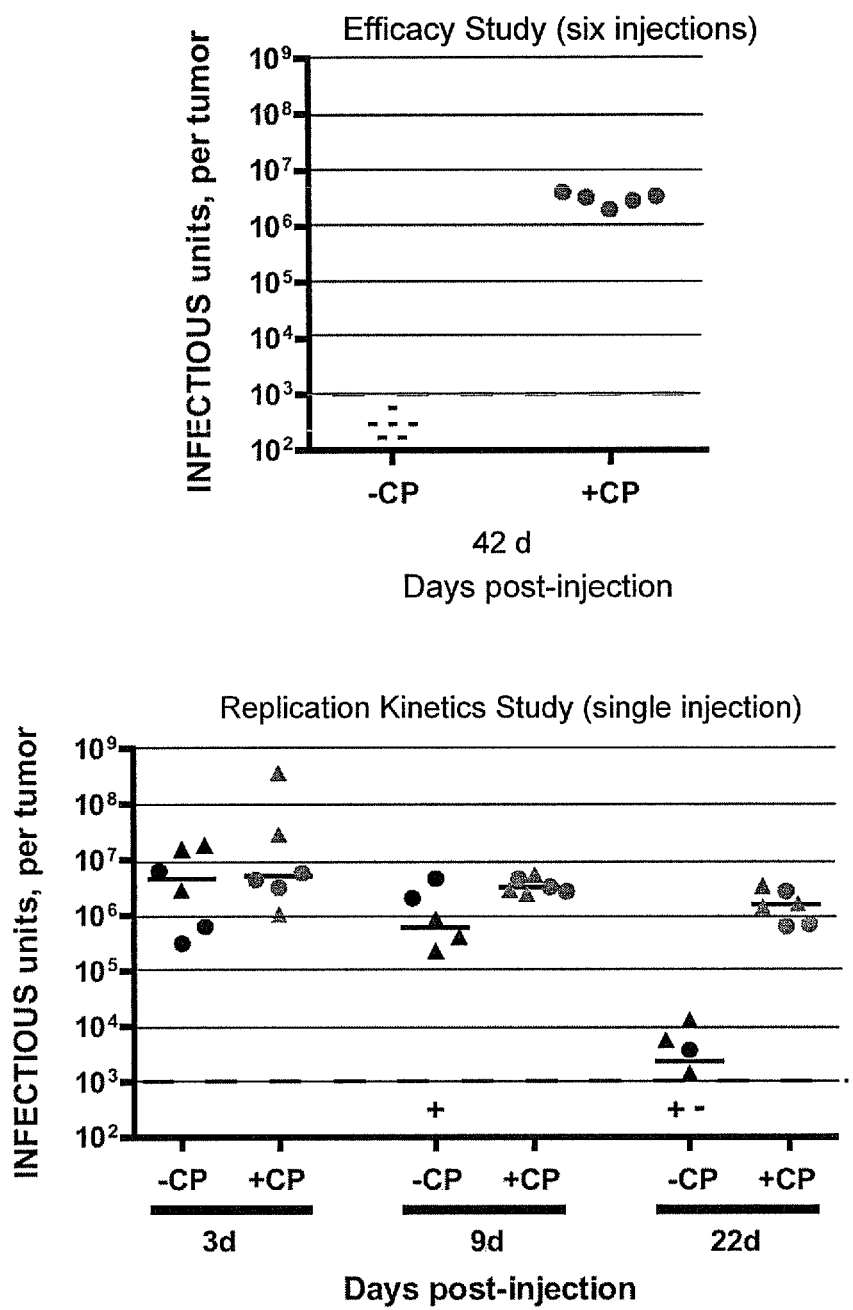
FIG. 6 is graphical representation of infectious virus titers of VRX-007 and Ad5 in tumors of hamsters treated or not treated with CP. In the left panel, corresponding to the Tumor Suppression Experiment, VRX-007 titers in the tumors of CP-treated and non-treated hamsters at the 42 day time point of FIG. 5. Titers were determined by $TCID_{50}$ assay. Each symbol is an individual hamster. In the right panel, corresponding to the Replication Kinetics Experiment, established tumors were injected once with $1\times10^{10}$ PFU of VRX-007 or Ad5 (n=3). Triangles are VRX-007 and circles are Ad5. The "+" sign indicates that virus was detected but was too low to quantify. The "−" sign indicates that virus was not detected.
Figure 7:
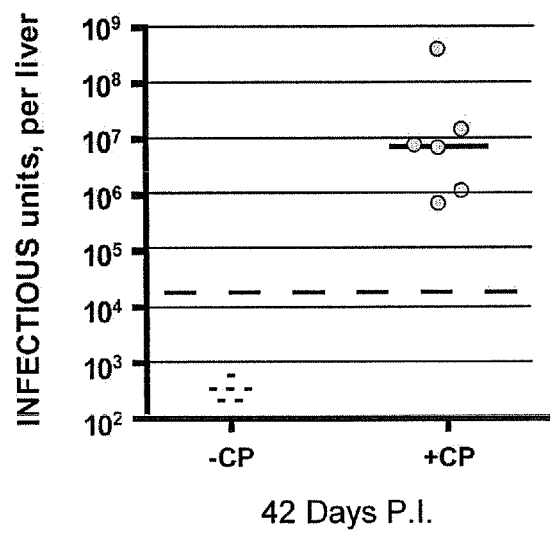
FIG. 7 is a graphical representation of immunosuppression by CP results in high levels of VRX-007 and Ad5 replication in the liver. Titers were determined by $TCID_{50}$ assay. Each symbol is an individual hamster. The "+" sign indicates CP treatment, the "−" indicates no CP treatment. In the left panel, corresponding to the Tumor Suppression Experiment, VRX-007 titers in the livers of CP-treated and non-treated hamsters at the 42 day time point of FIG. 5. No virus was detected in livers of the non-CP hamsters. In the right panel, corresponding to the Replication Kinetics Experiment, VRX-007 data are represented triangles and Ad5 data are represented by circles.
Figure 7:
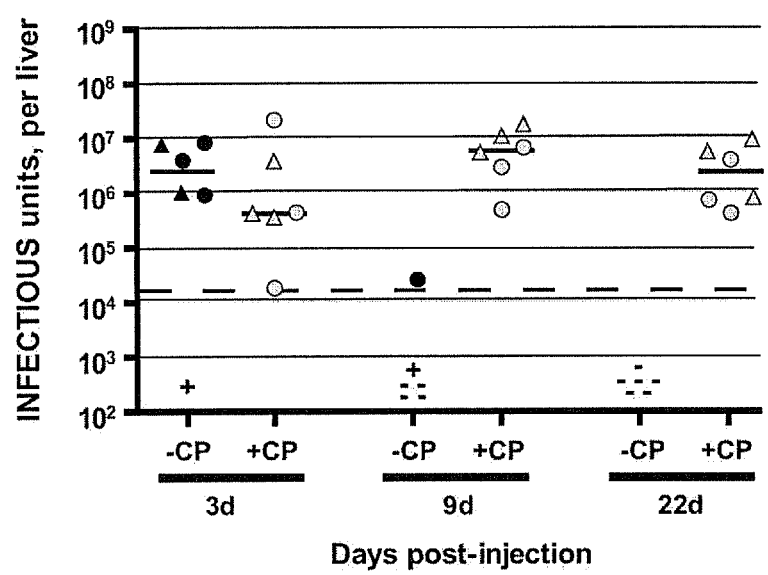
Figure 8:
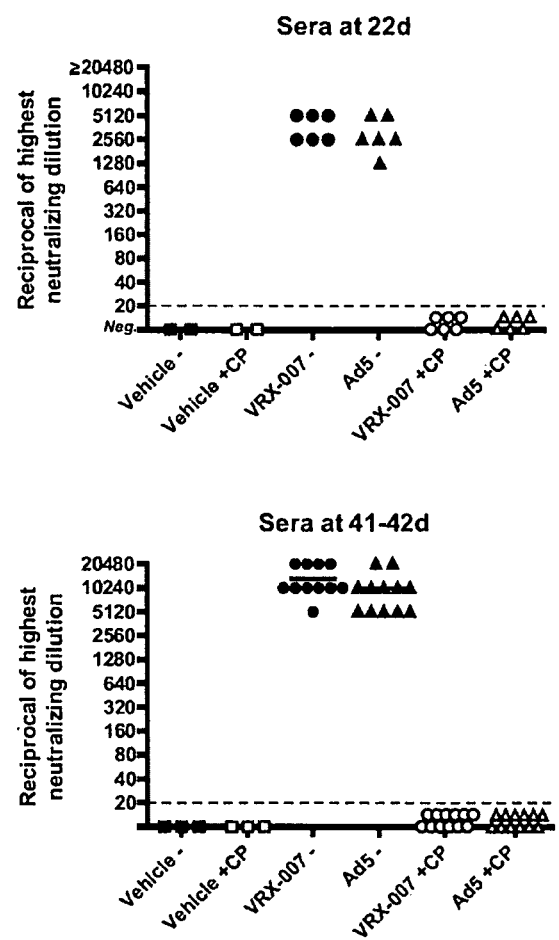
FIG. 8 is a graphical representation of CP blocks the neutralizing antibody response to VRX-007 and Ad5.

When analyzed by tissue culture infectious dose 50 ($TCID_{50}$) assay at the 42 day time point, there were $3.2 \times 10^6 \pm 3.5 \times 10^5$ (SEM) (range $2.0 \times 10^6$ to $4.1 \times 10^6$) infectious virus units of VRX-007 extracted from the tumors of the CP-treated hamsters (FIG. 6, left panel). No virus was obtained from tumors of hamsters not treated with CP. When the livers of these CP-treated hamsters were examined for infectious virus at the 42 day time point, roughly $10^7$ infectious units (range of about $10^6$ to about $10^9$) per liver were observed (FIG. 7, left panel). Virus was not detected by $TCID_{50}$ assay in the whole blood of any of the hamsters (not shown); this result indicates that the virus observed in the liver was the result of virus replication in the liver and not simply virus that was released from the tumor and entered the liver without replicating. Interestingly, virus was not detected in the livers of the hamsters not treated with CP (FIG. 7, left panel). When the antibody titer was examined, we found, as expected, no anti-Ad neutralizing antibody in the sera of the CP-treated hamsters whereas high levels were found in the sera of the non-CP hamsters (FIG. 8). These data indicate that the CP reduced the immune clearance of the vectors, and this resulted in increased vector replication in the tumors and enhanced suppression of tumor growth.

Further support for the conclusion that CP treatment leads to increased virus replication and persistence comes from the following non-limiting "Replication Kinetics" time course experiment. Hamsters with subcutaneous HaK rumors were treated with CP, then 4 days later tumors were injected once with buffer or with $1 \times 10^{10}$ PFU of VRX-007 or Ad5. CP was administered twice per week. Animals were sacrificed after 3, 9, and 22 days, and virus extracted from the tumors was quantitated by $TCID_{50}$ assay. As shown in FIG. 6 (right panel), there was roughly the same amount of VRX-007 and Ad5 in the tumors of both the CP- and non-CP hamsters at 3 days, about a log more of both viruses in the CP-hamsters at 9 days, and about 3 logs more at 22 days. The livers of these hamsters were also assayed for VRX-007 and Ad5. As shown in FIG. 7 (right panel), there were roughly $10^6$ to $10^7$ infectious virus particles per liver in the CP-treated hamsters at 9 and 22 days. In contrast, with the non-CP hamsters, only one liver had virus (about $3 \times 10^4$ infectious units) at 9 days and no livers had virus at 22 days.

Development of the hamster model to evaluate oncolytic Ad vectors and as a model of immunosuppression and anti-Ad drug efficacy requires that the toxicity of Ad in hamsters be understood. Thus, the MTD of VRX-007 was determined in hamsters; the MTD is the highest dose that does not cause overt toxicity (gross deviations from normal physiological and hematological values) and death.

In an early illustrative experiment, an exploratory study established that a single intrajugular injection of $1.9 \times 10^{10}$ PFU of VRX-007 did not cause gross pathology or death. Ad infectious units can be expressed as either plaque forming units (PFU) or as virus particles (vp). For most of our virus stocks, the vp:PFU ratio is about 10:1.

In the second non-limiting illustrative experiment, VRX-007 was injected into the jugular vein on three consecutive days. The four treatment groups were mock (lactated Ringer's injection solution), 1×, 3×, and 6×, with six animals per group. 1×, 3×, and 6× refer to the total dose administered relative to the dose of VRX-007 given in our first study. Animals in the 1× group received three doses of $6.3 \times 10^9$ PFU, animals in the 3× group received three doses of $1.9 \times 10^{10}$ PFU, and animals in the 6× group received two doses of $5.7 \times 10^{10}$ PFU. The cumulative doses administered were $1.9 \times 10^{10}$ PFU for the 1× group, $5.7 \times 10^{10}$ PFU for the 3× group, and $1.1 \times 10^{11}$ PFU for the 6× group.

Animals were monitored for change in weight, signs of morbidity, and mortality over a 14-day period. Blood was collected via orbital bleeds prior to the initial dose and on days 4, 9, and 14 in order to measure biochemical and hematological values as well as serum ALT and AST levels, two liver enzymes indicative of liver damage. All animals in the 6× group were either found dead or became moribund and were sacrificed by day three. At necropsy, these animals displayed moderate to severe liver pathology and possible signs of hemorrhage in the lungs, gastrointestinal tract, and the skin. Animals in the 3× group appeared much healthier than the 6× group. They lost 12% of body weight by day 3 but then gained weight at the same rate as the 1× and mock group to an increase of 15% by day 14 (not shown). One hamster died on day 7. Necropsy at day 4 showed mild to moderate liver pathology. At the 14-day sacrifice date, the two remaining hamsters had only mild liver pathology. Hamsters in the 1× group did not display any signs of morbidity throughout the 14-day study and no significant findings were observed at necropsy.

The ALT levels for each group generally correlated with the degree of gross liver pathology observed at necropsy, i.e. very high levels for the 6× group, quite high levels at day 4 for the 3× group which then returned to baseline, and very slight elevation at day 4 in the 1× group, illustrated in table 2 below. The AST data were similar. In the biochemical and hematologic evaluation, indications of liver toxicity were observed in the 3× group at day 4 but not at day 14. The mean alkaline phosphatase and bilirubin levels increased by 3-fold and 10-fold, respectively. Glucose, inorganic phosphate, calcium, albumin, and total protein levels decreased, while creatinine and blood urea nitrogen were unchanged. With the 1× group, there was a slight increase in alkaline phosphatase and decrease in albumin and total protein. Based on the morbidity and mortality observed, the MTD of VRX-007 when administered intravenously on three consecutive days to Syrian hamsters was the 1× dose ($1.9 \times 10^{10}$ PFU total). Since hamsters weigh about 90 g, the MTD expressed per kg is $2.1 \times 10^{11}$ PFU/kg.

Table 2, shown below, provides ALT levels from the second toxicity experiment. The levels of ALT in the serum at multiple timepoints are shown as the individual animal values as well as the group mean values. The IX values demonstrate that this dose did not cause significant liver toxicity. However, the 3× and 6× doses caused moderate to severe elevation of ALT in the serum.

| GROUP | Pre-bleed | Day 4 | Day 9 | Day 14 |
|---|---|---|---|---|
| Mock (#9) | 49 | 54 | NA | NA |
| Mock (#5) | 49 | 55 | NA | NA |
| Mock (#20) | 57 | 42 | 73 | 115 |
| Mock (#11) | 54 | 58 | 75 | 61 |
| Mock (#6) | 57 | 56 | 54 | 48 |
| Mock mean | 53 | 53 | 67 | 75 |
| 1X (#23) | 67 | 79 | NA | NA |
| 1X (#16) | 70 | 83 | NA | NA |
| 1X (#21) | 66 | 96 | NA | NA |
| 1X (#14) | 50 | 160 | 51 | 58 |
| 1X (#13) | 50 | 61 | 61 | 67 |
| 1X (#12) | 57 | 92 | 55 | 51 |
| 1X mean | 60 | 95 | 56 | 59 |
| 3X (#8) | 44 | 5750 | NA | NA |
| 3X (#10) | 82 | 1106 | NA | NA |
| 3X (#19) | 69 | 2650 | NA | NA |
| 3X (#18) | 42 | 5680 | NA | NA |
| 3X (#4) | 50 | 7150 | 317 | 191 |
| 3X (#1) | 62 | 126 | 58 | 47 |
| 3X mean | 58 | 3744 | 188 | 119 |
| 6X (#2) | 55 | NA | NA | NA |
| 6X (#15) | 50 | *16150 | NA | NA |
| 6X (#24) | 52 | NA | NA | NA |
| 6X (#3) | 62 | *17490 | NA | NA |
| 6X (#7) | 46 | **8530 | NA | NA |
| 6X (#17) | 61 | NA | NA | NA |
| 6X mean | 54 | 14057 | NA | NA |

*ALT at time of sacrifice (Day 2)
**ALT at time of sacrifice (Day 3)

The third non-limiting illustrative experiment was a more extensive toxicology study, designed in consultation with the FDA. A single jugular vein injection of three different doses of VRX-007 was administered: high ($1.9 \times 10^{10}$ PFU, which is the MTD determined in an earlier toxicology study), medium ($3 \times 10^8$ PFU), and low ($3 \times 10^7$ PFU). Controls were wild-type Ad5 and AdCMVpA (an E1A-, E1B-minus replication-defective Ad vector with the CMV promoter but no transgene) at the high dose, and vehicle. 180 hamsters (90 males and 90 females) were used with 5 animals per sex per group, and toxicity was assessed on days 2, 7, and 29 following injection. Animals were weighed, pre-bled, bled again at time of harvest, necropsied, and scored for gross pathology. Most tissues were collected, weighed, and stored in formalin for subsequent histopathology and IHC. Blood was collected and subjected to serum chemistry and hematological analyses.

Figure 9:
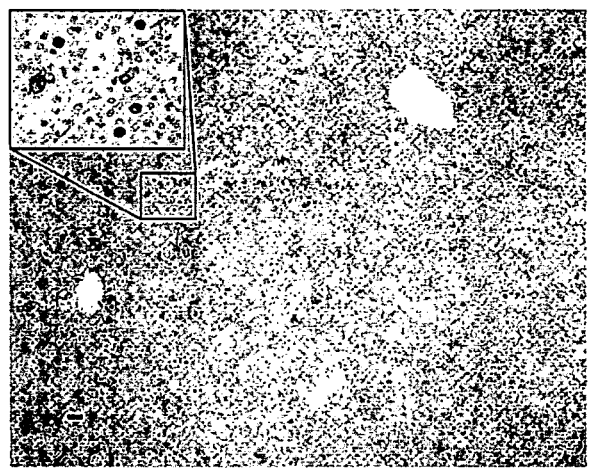
FIG. 9 is a picture of immunohistochemistry of liver section from hamsters injected with VRX-007.

The toxicity report draws to the following conclusions: The high dose of VRX-007 and Ad5 caused transient liver toxicity as evidenced by gross pathology and about 2-4-fold elevated levels of liver enzymes at 7 days post injection. Infection of scattered liver cells was shown by immunohistochemistry for the Ad fiber protein (a component of the virus particle) (FIG. 9). The sections were prepared 2 days post injection. The primary antibody is against fiber, an Ad "late" capsid protein. No staining was observed in livers of hamsters injected with the replication-defective AdCMVpA vector (not shown). In FIG. 9, the magnification is 100× for the overall image and 400× for the inset. The toxicity resolved by 29 days, with the exception of one out of five animals in both the Ad5- and the high dose VRX-007-injected groups which were found dead at 4 days. No significant pathology was observed with the vehicle-, AdCMVpA-, low dose VRX-007-, or mid dose VRX-007-injected animals. The high dose of all viruses induced an immune response: at 7 days, the spleens of the animals in these groups were about 3-fold larger than the spleens of the control animals, and the counts of various white blood cell types (e.g. lymphocytes) were elevated about 2-3 fold. These symptoms resolved by 29 days. The hamster sera had high antibody levels to Ad as assayed by immunofluorescence. The conclusion from this study is that the "No Observed Adverse Effect Level" (NOAEL) was $3 \times 10^8$ PFU. Although this study was not designed to determine the MTD for a single injection of VRX-007 or Ad5, it may be concluded that it is higher than $3 \times 10^8$ PFU (the NOAEL) and lower than $1.9 \times 10^{10}$ PFU (the high dose) for which some animals died.

An extensive pharmacokinetic and biodistribution study, which was designed in consultation with the FDA, has also been conducted. A total of 200 hamsters (5 hamsters per sex, 5 per treatment group, 5 per time point) were administered a single jugular vein injection of vehicle or $1.9 \times 10^{10}$ PFU of VRX-007, Ad5, or AdCMVpA. Time points were taken at 2, 7, 29, 92, and 372 days. Blood, adrenals, brain, bone marrow, heart, kidney, lung, liver, spleen, lymph nodes, and gonads were collected. Tissues were homogenized and DNAs were extracted and analyzed for VRX-007, Ad5, or AdCMVpA DNA using qPCR. The remaining portion of the liver, lung, and testes homogenates was titered for infectious virus using a $TCID_{50}$ assay in HEK293 cells (AdCMVpA will replicate on HEK293 cells).

Figure 10:
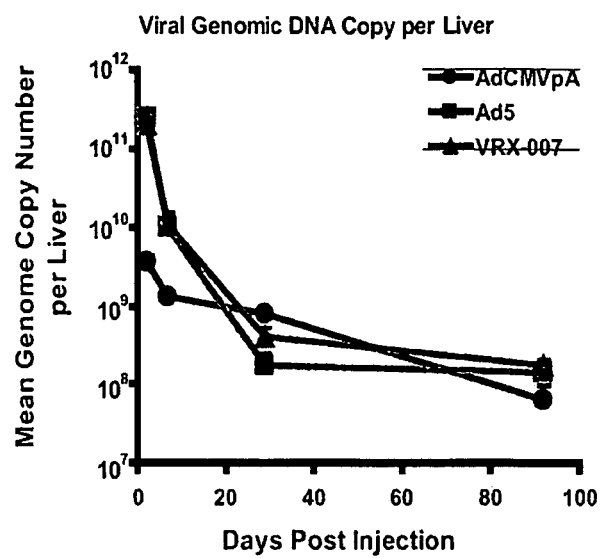
FIG. 10 is a graphical representation of a Pharmacokinetics/Biodistribution study with viral genomic copies per liver and infections particles per liver.
Figure 10:
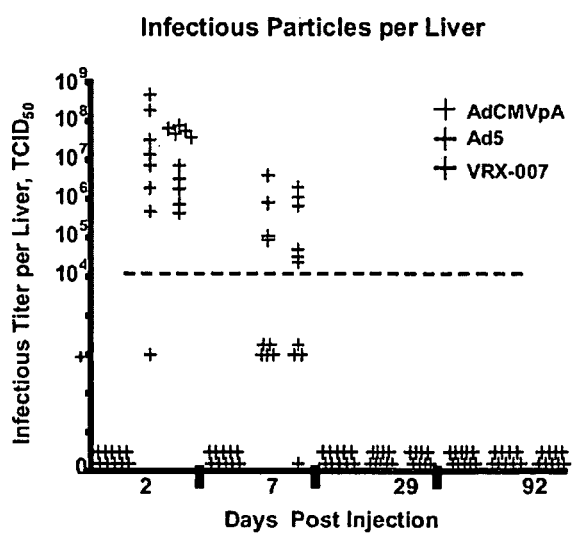

The primary target was the liver. At 2 days, there were on average $2-3 \times 10^{11}$ genomic copies per liver of VRX-007 and Ad5, and about two logs less of AdCMVpA shown in FIG. 10 the left panel. The genome copy number dropped over time such that the VRX-007, Ad5, and AdCMVpA levels were similar at 29, 92, and 372 days. There were roughly $10^7$ infectious particles ($3 \times 10^5$ to $3 \times 10^8$ range) per liver of VRX-007 and Ad5 at day 2 shown in FIG. 10 the right panel. Titers of VRX-007 and Ad5 dropped at day 7, very roughly by a couple of logs, and no virus was detected at days 29 or 92. AdCMVpA was never detected at any time point. These results establish that VRX-007 and Ad5 replicate in the liver, that they replicate to a similar extent, and that the infectious virus was cleared by 29 days. Replication in the liver is consistent with the liver toxicity as seen in the toxicology study.

It was previously shown that VRX-007 and Ad5 replicate in the liver, lungs, and other organs following intravenous administration into immunocompetent animals. The primary organ of replication is the liver. These viruses also replicate in hamster tumors following intratumoral injection. When doses higher than the MTD ($1.9 \times 10^{10}$ PFU total) are administered, transient liver toxicity occurs, and if the dose is about 6× the MTD, most of the hamsters die in a few days. These viruses also replicate in hamster tumors following intratumoral injection. An adaptive immune response develops in as little as about 10 days as indicated by the development of antibodies including neutralizing antibodies. It was herein shown that immunosuppression with CP prior to administration of the virus to hamsters blocks the immune response and results in high and prolonged levels of virus replication in tumors, the liver, and probably other organs.

It is remarkable that these immunosuppressed hamsters can sustain such high levels of virus in the livers. In the tumor suppression experiment described in FIG. 4, the virus titers in the livers ranged from $10^6$ to as high as $10^9$ (FIG. 7, left panel). In the "Reprication Kinetics" experiment, the titers in the liver were $10^6$ to $10^7$ PFU (FIG. 7, right panel). It is quite possible that the titers could have gone higher if the experiments were continued past 42 days. Further, it is highly likely that there was virus in other organs of these CP-immunosuppressed hamsters, because VRX-007 and Ad5 can infect many organs following intravenous injection. These high and sustained levels of replication in the immunosuppressed hamsters are very similar to the disseminated Ad infections that occur in immunosuppressed human transplant patients, especially the pediatric stem cell transplant patients.

Thus, the instant immunosuppressed hamster model affords for the first time the opportunity to study disseminated Ad infections in an animal model in which the animal is permissive for Ad replication. Further, this model allows anti-Ad drugs to be evaluated under conditions where the virus is replicating efficiently.

HDP-CDV as Example Anti-Adenoviral in CP Syrian Hamster Model

Figure 11:
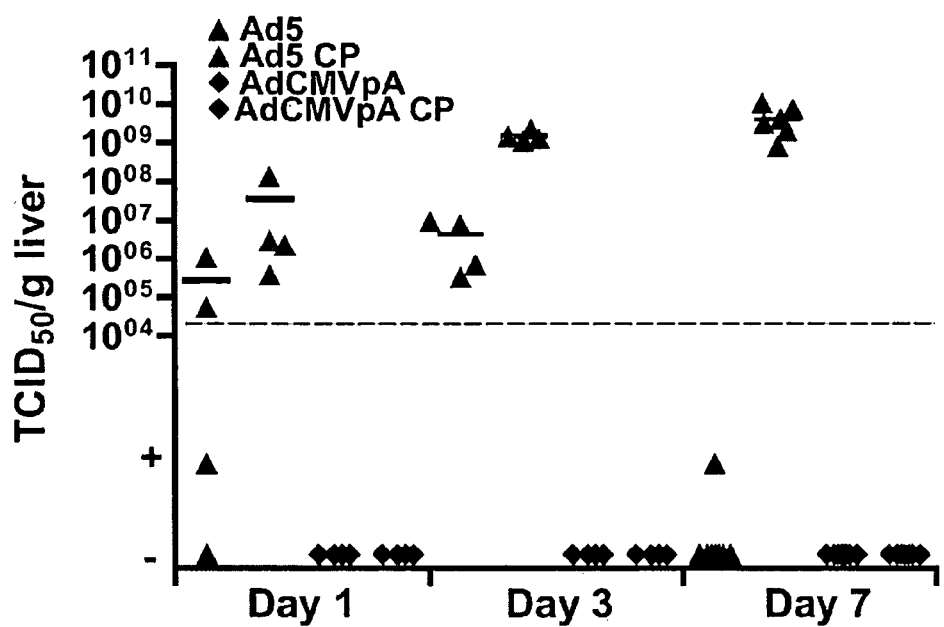
FIG. 11 is a graphical representation of how immunosuppression enhances the replication of Ad5 in the livers of Syrian hamsters.

The instant immunosuppressed Syrian hamster system was tested for its ability to assess the anti-adenoviral activity of cidofovir. A modified form of the antiviral cidofovir, HDP-CDV, was used in this example. FIG. 11 demonstrates that CP-treated Syrian hamsters permits enhanced reprication of Ad5 in liver, and is therefore a useful model for human immunosuppressed patients. Syrian hamsters were injected intravenously with $1.9 \times 10^{12}$ vp/kg ($3 \times 10^{10}$ PFU total) of Ad5 or a replication defective adenovirus (AdCMVpA). Half of the animals in both groups were immunosuppressed with CP. At the indicated time points, the animals were sacrificed, and the infectious virus in the liver was titered on a human cell line that allows for the replication of both Ad5 and AdCMVpA. The dashed line represents the limit of calculability.

Figure 12:
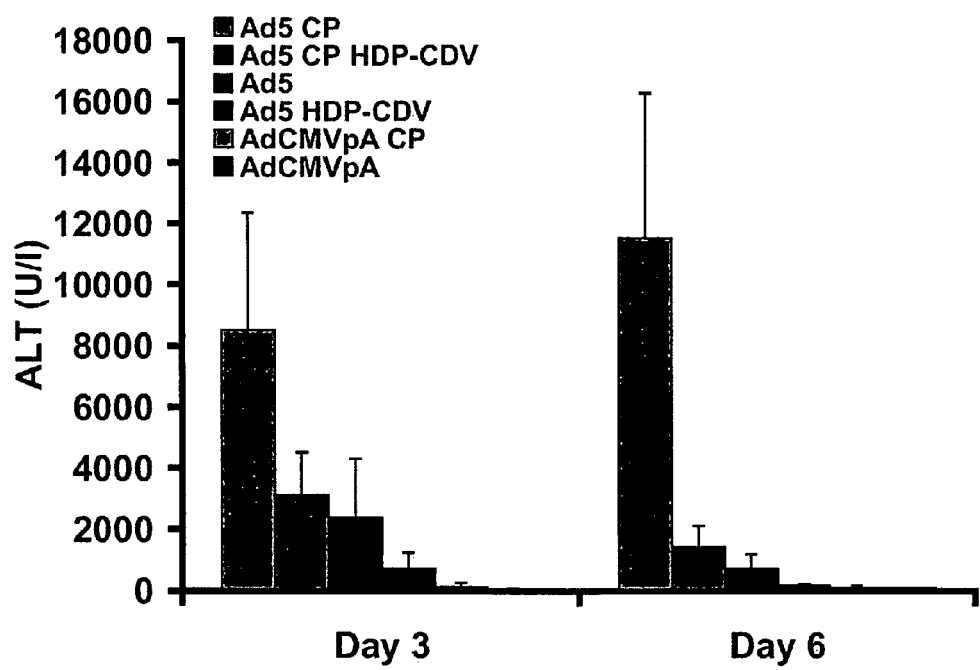
FIGS. 12A-12D are graphical representations illustrating HDP-CDV decreasing adenovirus induced liver toxicity and viral load.
Figure 12:
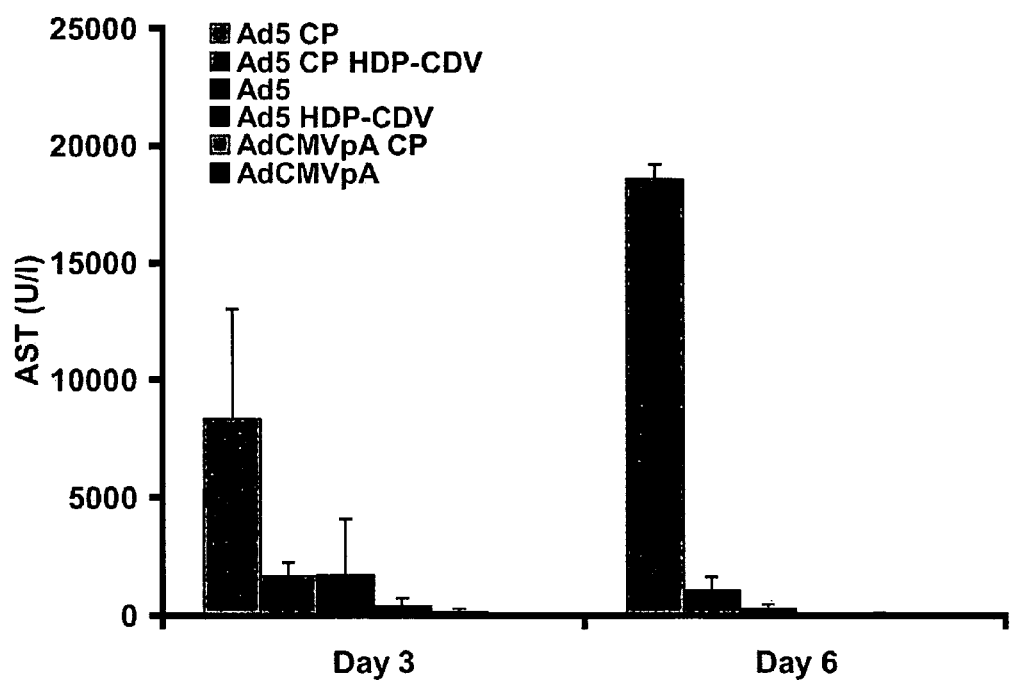
Figure 12:
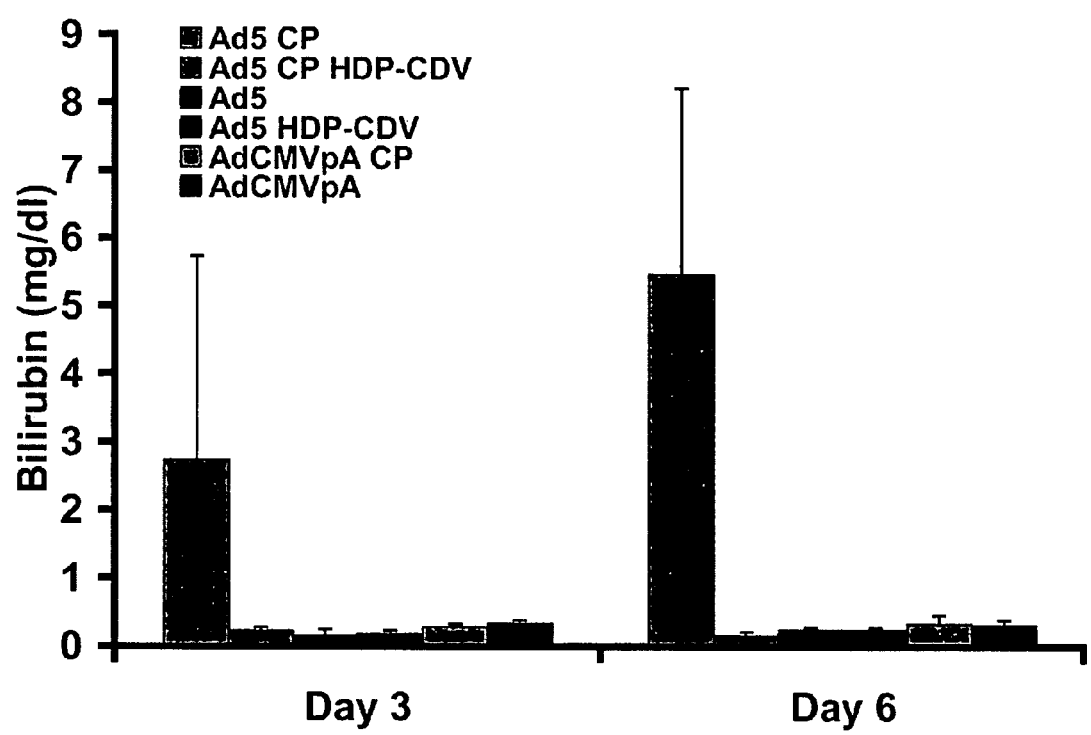
Figure 12:
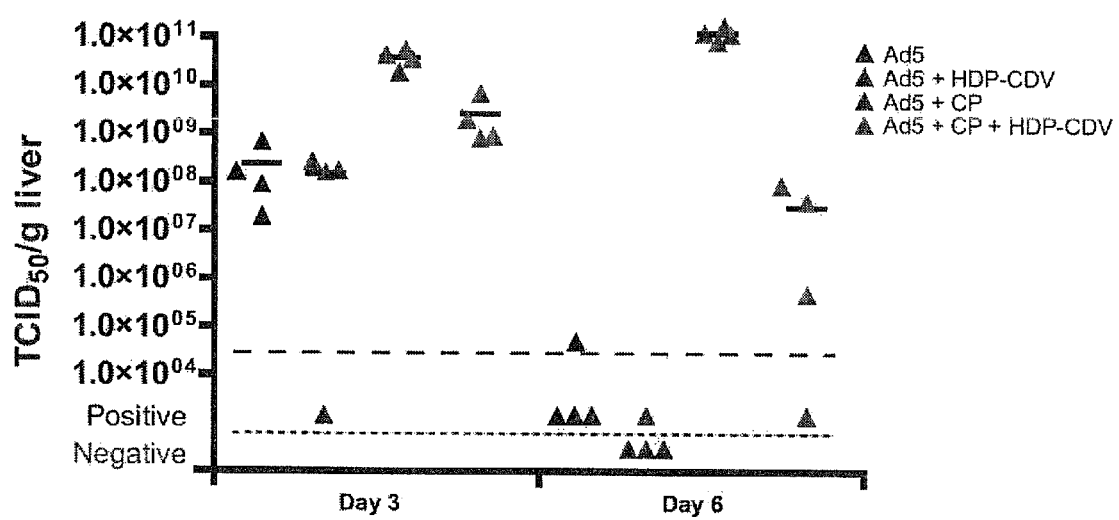

FIG. 12 clearly demonstrates that HDP-CDV effectively and significantly reduces liver toxicity as well as adenoviral loads in Syrian hamsters that were both normal and immunosuppressed, thus supporting the utility of the invention for identifying antiadenoviral drugs useful in the treatment of immunosuppressed individuals. Syrian hamsters (females, average weight 98 g) were immunosuppressed with twice weekly injections of cyclophosphamide (starting on Day −6; 140 mg/kg i.p. for the first dose, then 100 mg/kg). On Day 0, the animals were injected intravenously (into the jugular vein) with $1.9 \times 10^{12}$ vp/kg (ca. $3 \times 10^{10}$ PFU/animal) of Ad5 or AdCMVpA, and half of them were treated with HDPCDV (2.5 mg/kg via oral gavage daily for 6 days, starting on Day −1). On Days 3 and 6, hamsters were sacrificed and their sera were analyzed for transaminases (panel A=ALT; panel B=AST) and bilirubin (panel C). Infectious virus titers in the liver were determined, by $TCID_{50}$ assays; the dashed line in the graph marks the threshold of quantifiability, horizontal lines represent group means, n-4, except for clinical chemistry for the Ad5 CP group on Day 6 (n=2); the error bars represent standard deviation. No infectious virus was detected in the liver of any of the AdCMVpA-injected animals (panel D).

Figure 13:
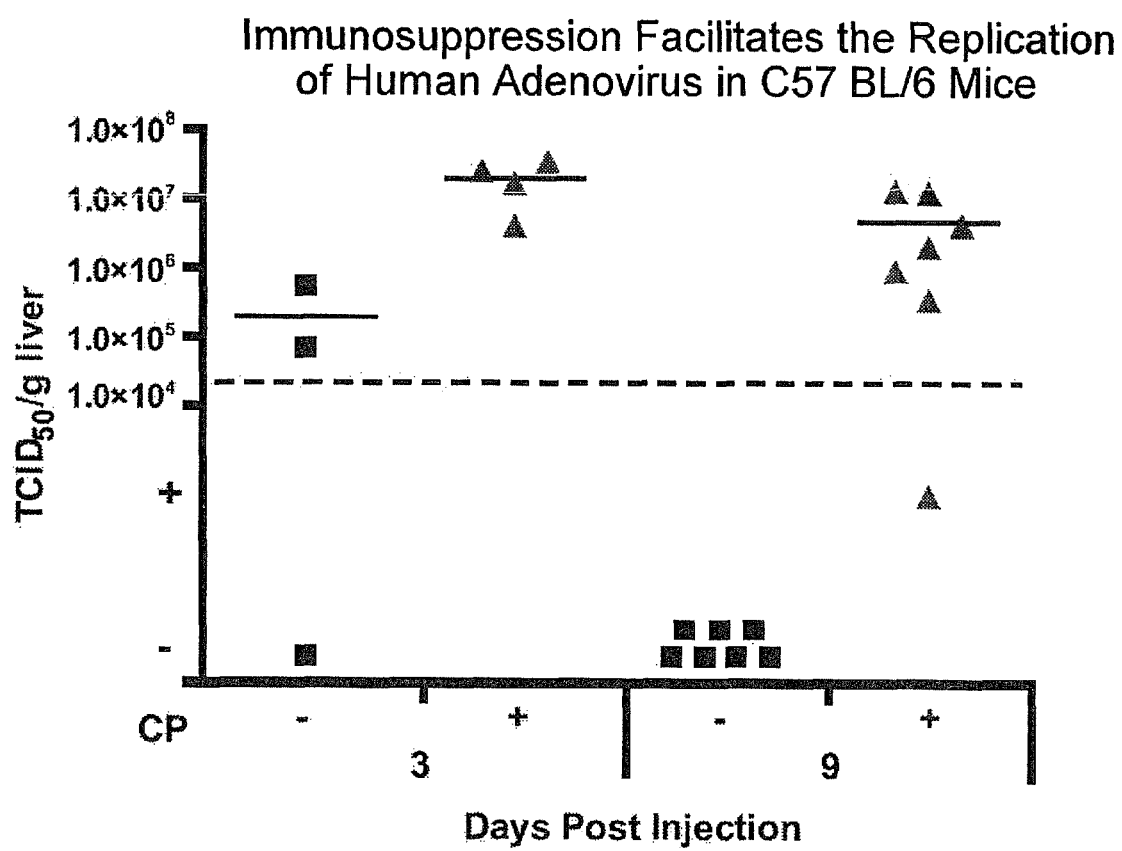
FIG. 13 is a graphical representation of immunosuppression increasing the replication of Ad5 in mice.

FIG. 13 graphically illustrates the data for immunosupressed increases the replication of human adenovirus serotype 5 in mice. Immunocompetent mice and mice immunosuppressed with CP were injected intravenously with $1.5 \times 10^{11}$ vp/kg of Ad5. At the indicated times, mice were sacrificed and infectious virus titers in the liver were determined.

Figure 14:
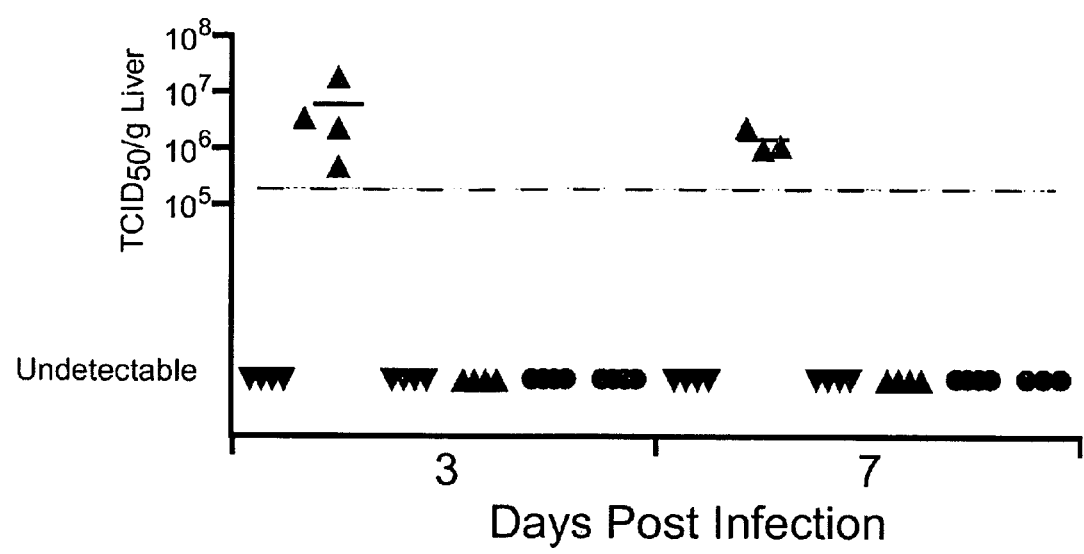
FIG. 14 is a graphical representation of HDP-CDV suppressing the replication of Ad 5 in immunosuppressed mice.

FIG. 14 graphically illustrates the data for HDP-CDV suppressing the replication of human adenovirus serotype 5 in immunosuppressed mice. Immunocompetent mice and mice immunosuppressed with CP were injected intravenously with $1.5 \times 10^{11}$ vp/kg of Ad5 or AdCMVpA, a replication defective adenovirus. Half of the animals in each group were treated via oral gavage with daily doses of 2.5 mg/kg of HDP-CDV, starting a day before virus injection. At the indicated times, mice were sacrificed and infectious virus titers in the liver were determined.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. A method for screening an anti-adenovirus agent in a Syrian hamster systemic infection model comprising the steps of:
    (a) infecting a Syrian hamster immunosuppressed by cyclophosphamide with a human adenovirus Species C serotype replicable in said hamster by intravenous injection and maintaining said hamster for a time period sufficient for said human adenovirus to replicate;
    (b) treating said immunosuppressed, infected hamster with a candidate anti-adenovirus agent;
    (c) maintaining said treated, infected hamster for a time sufficient for said candidate anti-adenovirus agent to act; and
    (d) determining the viral load in or pathology of an organ of said hamster of step (c) as compared to that of an otherwise same, infected Syrian hamster not treated with the candidate anti-adenovirus agent;
whereby a treated hamster having a lower organ viral load or lesser organ pathology, as compared to an untreated hamster, indicates an efficacious treatment.

2. The method claim 1, further comprising the step of immunosuppressing said hamster prior to step (a).

3. The method of claim 1, wherein step (d) comprises assessing organ viral load with PCR.

4. The method of claim 1, wherein said organ is liver or lung.

5. The method of claim 1, wherein assessing viral load comprises titering virus from an organ sample.

6. The method claim 1, wherein assessing organ pathology comprises immunohistochemistry.

7. The method claim 1, wherein assessing organ pathology comprises assessing liver pathology with blood or serum levels of the liver enzymes alanine aminotransferase (ALT) and aspartate aminotransferase (AST).

* * * * *

UNITED STATES PATENT AND TRADEMARK OFFICE
CERTIFICATE OF CORRECTION

| | |
|---|---|
| PATENT NO. | : 9,011,820 B2 |
| APPLICATION NO. | : 12/124807 |
| DATED | : April 21, 2015 |
| INVENTOR(S) | : Karoly Toth and William S. M. Wold |

It is certified that error appears in the above-identified patent and that said Letters Patent is hereby corrected as shown below:

In the specification,

In column 1, line 8, delete "60/939,194" and insert --60/939,184--.

In the claims,

In claim 2, column 16, line 42, insert --of-- between "method" and "claim".

In claim 2, column 16, lines 42-43, delete "further comprising the step of immunosuppressing said hamster" and insert --wherein the Syrian hamster is immunosuppressed by cyclophosphamide--.

Signed and Sealed this
Sixth Day of October, 2015

Michelle K. Lee
*Director of the United States Patent and Trademark Office*